United States Patent
Bar-Ziv et al.

(10) Patent No.: US 12,172,159 B2
(45) Date of Patent: Dec. 24, 2024

(54) USE OF ELECTRIC FIELD GRADIENTS TO CONTROL GENE EXPRESSION

(71) Applicant: Yeda Research and Development Co. Ltd., Rehovot (IL)

(72) Inventors: Roy Bar-Ziv, Rehovot (IL); Alexandra Tayar, Rehovot (IL); Shirley Shulman Daube, Rehovot (IL); Yuval Efrath, Rehovot (IL); Michael Levy, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1128 days.

(21) Appl. No.: 17/029,228

(22) Filed: Sep. 23, 2020

(65) Prior Publication Data

US 2021/0031193 A1 Feb. 4, 2021

Related U.S. Application Data

(63) Continuation of application No. PCT/IL2019/050367, filed on Mar. 28, 2019.

(60) Provisional application No. 62/649,605, filed on Mar. 29, 2018.

(51) Int. Cl.
*B01L 3/00* (2006.01)
*C12N 13/00* (2006.01)
*C12N 15/10* (2006.01)
*G01N 27/447* (2006.01)

(52) U.S. Cl.
CPC ..... *B01L 3/502715* (2013.01); *B01L 3/50273* (2013.01); *C12N 13/00* (2013.01); *C12N 15/1075* (2013.01); *G01N 27/447* (2013.01); *B01L 2300/0816* (2013.01); *B01L 2300/0867* (2013.01); *B01L 2400/0424* (2013.01)

(58) Field of Classification Search
CPC ........... B01L 3/502715; B01L 3/50273; B01L 2300/0816; B01L 2300/0867; B01L 2400/0424; C12N 13/00; C12N 15/1075; G01N 27/447; C12Q 1/6844; C12Q 1/6897
See application file for complete search history.

(56) References Cited

U.S. PATENT DOCUMENTS

| | | | |
|---|---|---|---|
| 8,449,837 B2 | 5/2013 | Levchenko et al. | |
| 8,592,221 B2 | 11/2013 | Fraden et al. | |
| 2016/0243547 A1* | 8/2016 | Bar-Ziv | B01J 19/0093 |

(Continued)

FOREIGN PATENT DOCUMENTS

| | | |
|---|---|---|
| WO | WO 2008/090557 | 7/2008 |
| WO | WO 2015/052717 | 4/2015 |
| WO | WO 2019/186569 A9 | 10/2019 |

OTHER PUBLICATIONS

International Preliminary Report on Patentability Dated Oct. 8, 2020 From the International Bureau of WIPO Re. Application No. PCT/IL2019/050367. (7 Pages).

(Continued)

*Primary Examiner* — C. Sun

(57) ABSTRACT

Methods of controlling biological processes by altering the electric field gradient in a test chamber are disclosed. A portion of a surface of the test chamber is attached to at least one immobilized component of the biological process. Microfluidic devices capable of same are also disclosed.

7 Claims, 18 Drawing Sheets
(15 of 18 Drawing Sheet(s) Filed in Color)
Specification includes a Sequence Listing.

(56) References Cited

U.S. PATENT DOCUMENTS

2016/0266105 A1* 9/2016 Ismagilov ............. B01L 3/5023
2017/0241888 A1* 8/2017 Chu ........................ C12Q 1/04

OTHER PUBLICATIONS

International Search Report and the Written Opinion Dated Jun. 17, 2019 From the International Searching Authority Re. Application No. PCT/IL2019/050367. (14 Pages).

Hölzel et al. "Trapping Single Molecules by Dielectrophoresis", Physical Review Letters, 95(12): 128102-1-128102-4, Sep. 16, 2005.

Karzbrun et al. Programmable On-Chip DNA Compartments as Artificial Cells Eyal Karzbrun1, Science, 345(6198): 829-832, Aug. 15, 2014.

Mei et al. "Cell-Free Protein Synthesis in Microfluidic Array Device", Biotechnology Progress, 23(6): 1305-1311, Nov. 1, 2007.

Nakano et al. "Protein Dielectrophoresis: Advances, Challenges, and Applications", Electrophoresis, 34(7): 1085-1096, Apr. 2013.

Tuukkanen et al. "Trapping of 27 BP-8 KBP DNA and Immobilization of Thiol-Modified DNA Using Dielectrophoresis", Nanotechnology, 18(29): 295204-1-295204-10, Published Online Jun. 20, 2007.

Communication Pursuant to Article 94(3) EPC Dated Sep. 8, 2023 From the European Patent Office Re. Application No. 19717617.5. (3 Pages).

\* cited by examiner

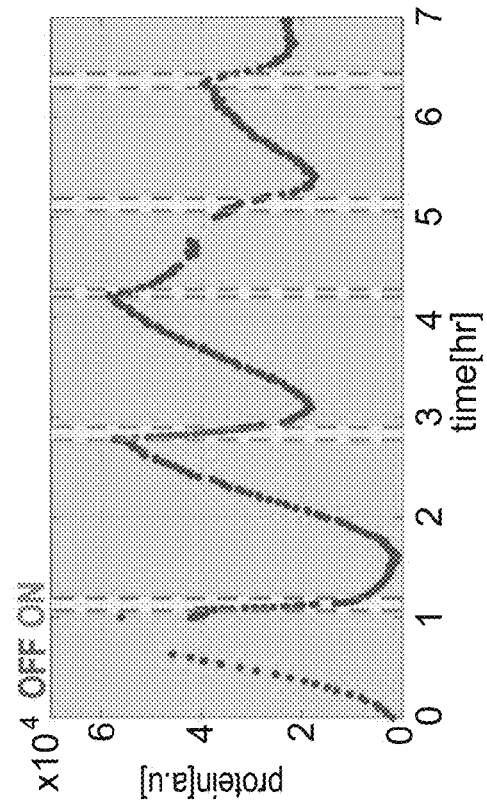
FIG. 1A
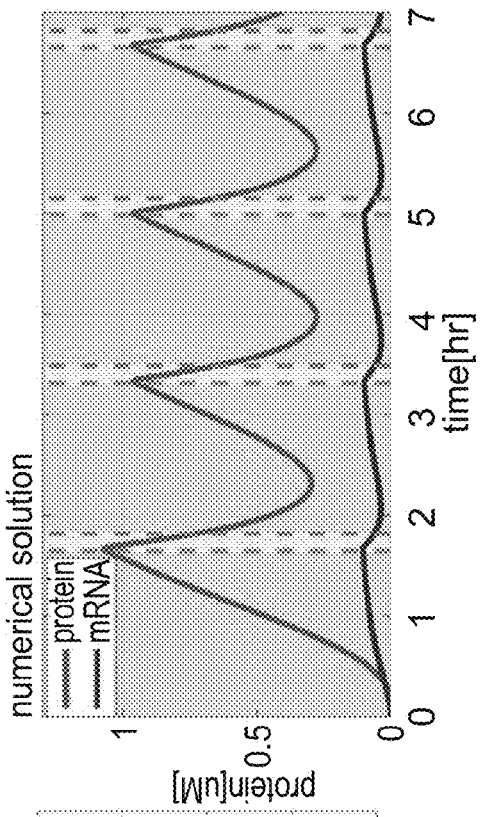
FIG. 1B
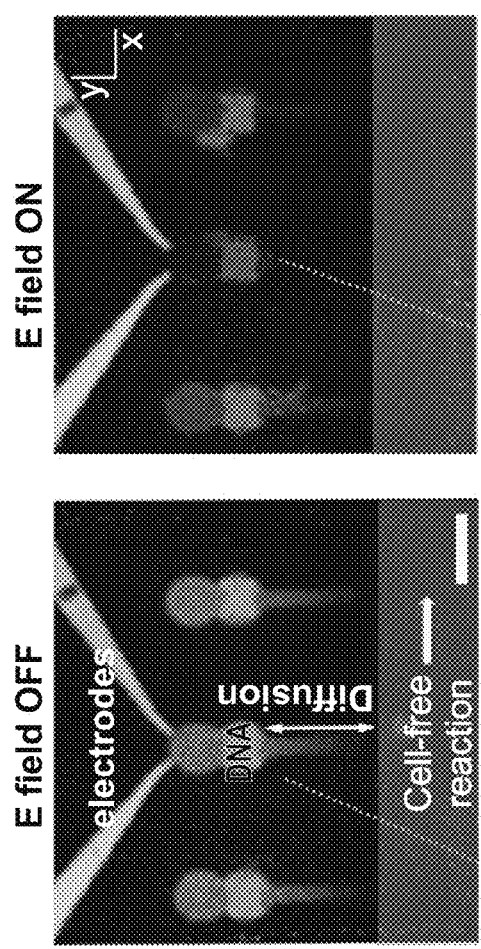
FIG. 1C
FIG. 1D
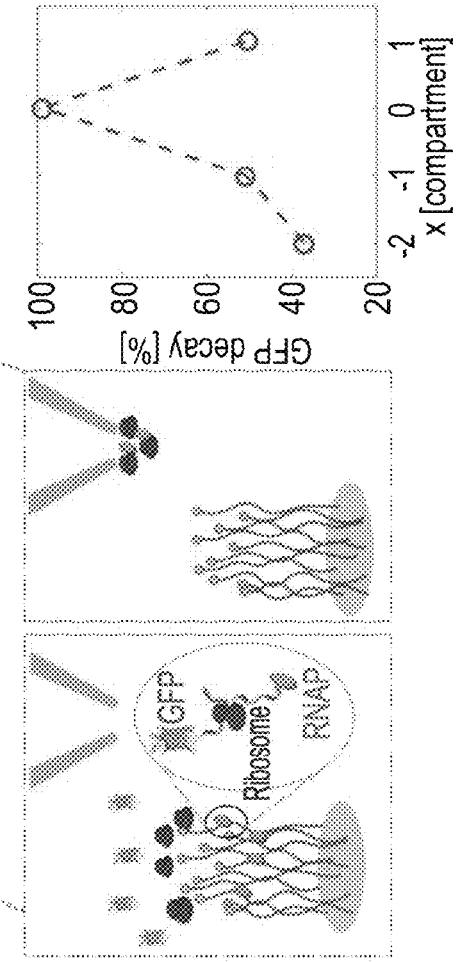
FIG. 1E

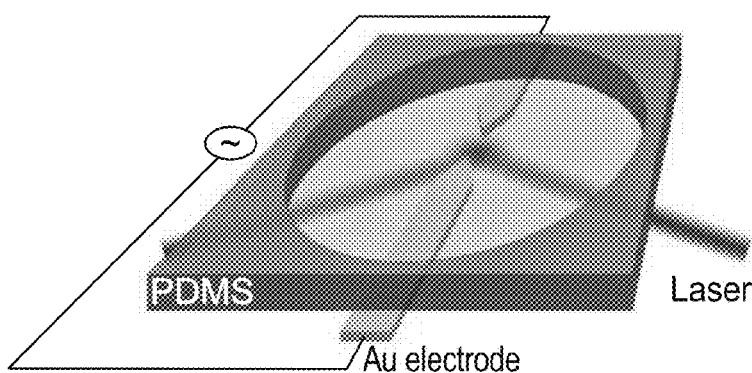
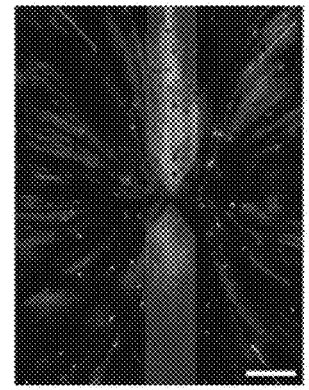
FIG. 2A  FIG. 2B
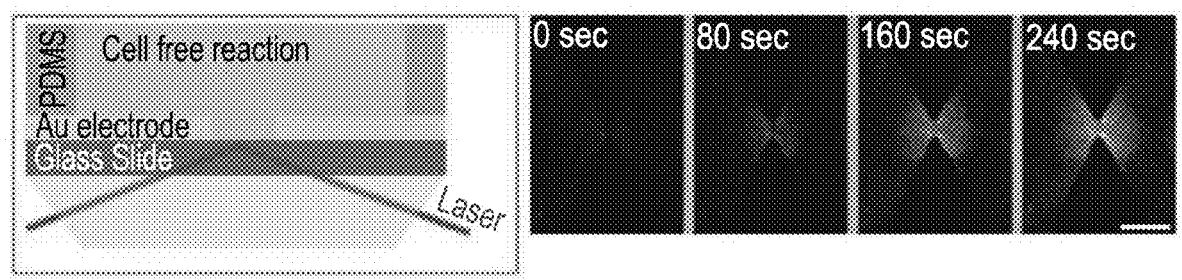
FIG. 2C
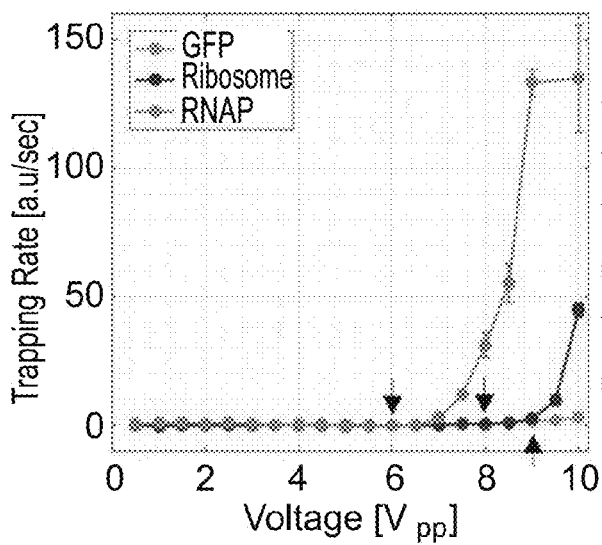
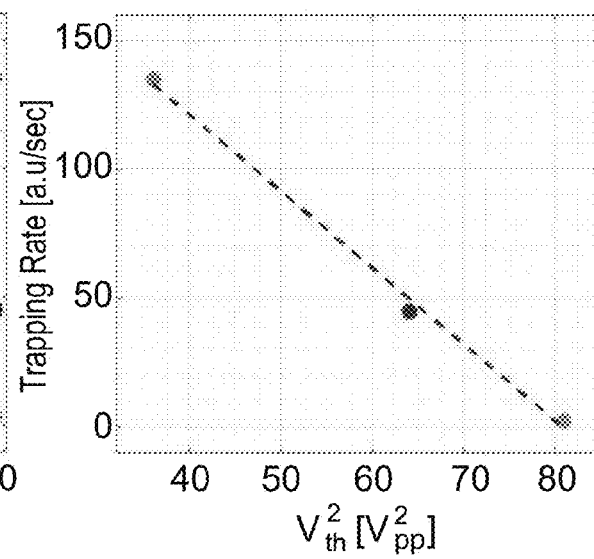
FIG. 2D  FIG. 2E

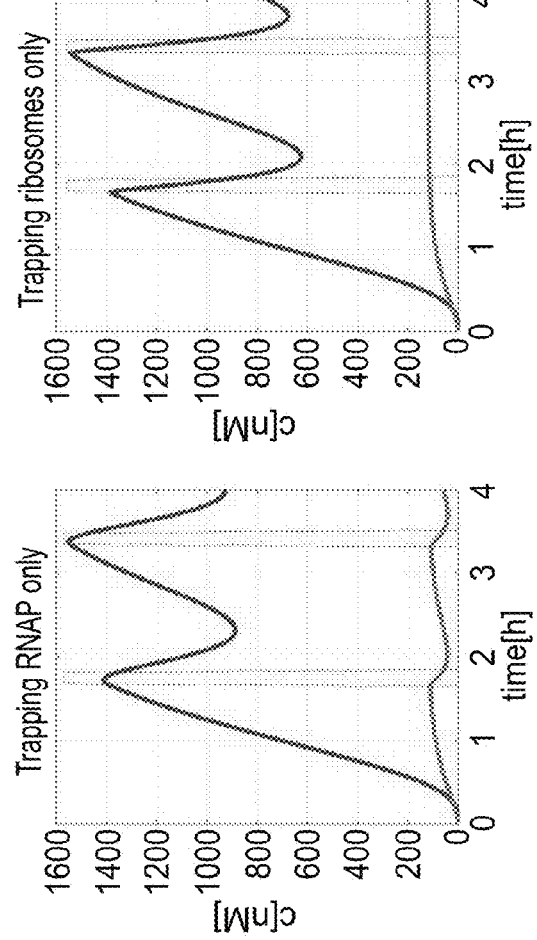
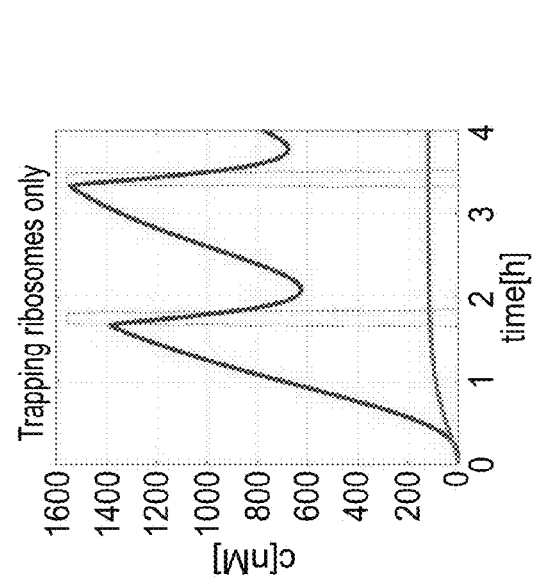
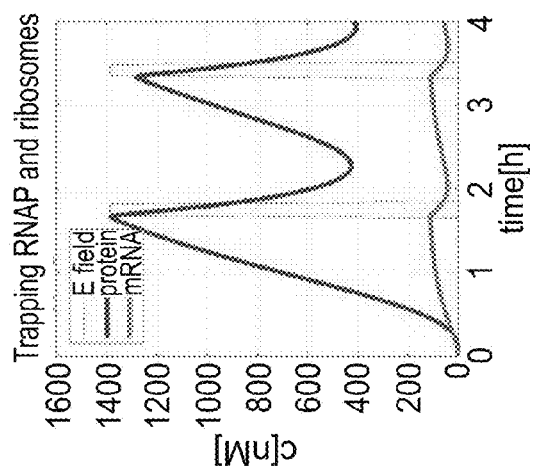
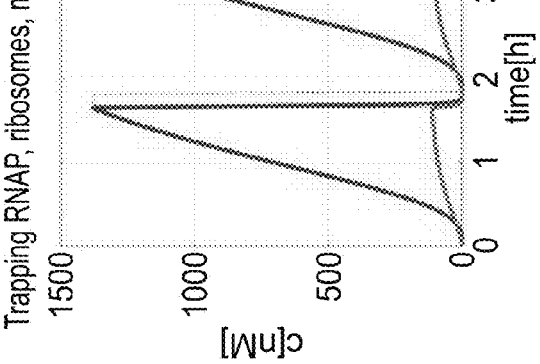
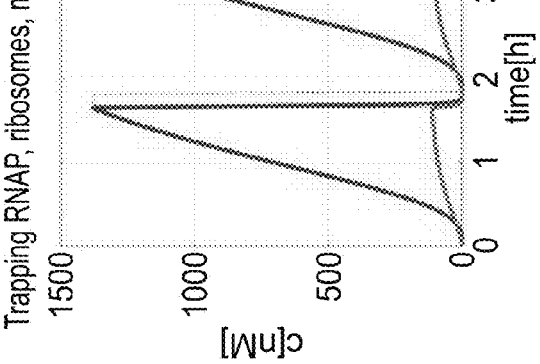
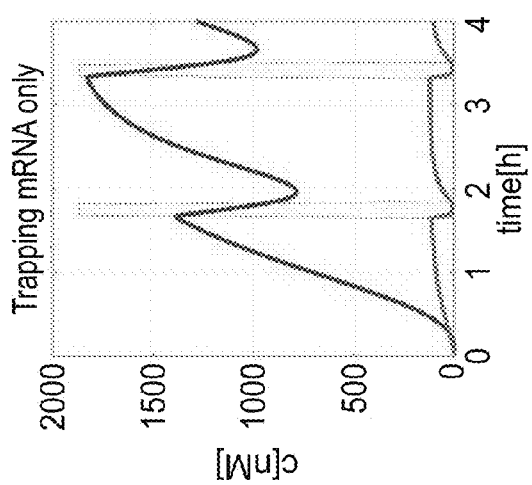

USE OF ELECTRIC FIELD GRADIENTS TO CONTROL GENE EXPRESSION

RELATED APPLICATIONS

This application is a US Continuation of PCT Patent Application No. PCT/IL2019/050367 having international filing date of Mar. 28, 2019 which claims the benefit of priority under 35 USC § 119(e) of U.S. Provisional Patent Application No. 62/649,605 filed on Mar. 29, 2018. The contents of the above applications are all incorporated by reference as if fully set forth herein in their entirety.

SEQUENCE LISTING STATEMENT

The ASCII file, entitled 83894SequenceListing.txt, created on Sep. 29, 2020, comprising 904 bytes, submitted concurrently with the filing of this application is incorporated herein by reference.

FIELD AND BACKGROUND OF THE INVENTION

The present invention, in some embodiments thereof, relates to use of electric field gradients to control biological reactions and, more particularly, but not exclusively, to control gene expression.

Recently, there have been concerted efforts to develop and manufacture microfluidic systems to perform various chemical and biochemical analyses and syntheses, both for preparative and analytical applications. The goal to make such devices arises because of the significant benefits that can be realized from miniaturization with respect to analyses and syntheses conducted on a macro scale. Such benefits include a substantial reduction in time, cost and the space requirements for the devices utilized to conduct the analysis or synthesis.

Additionally, microfluidic devices have the potential to be adapted for use with automated systems, thereby providing the additional benefits of further cost reductions and decreased operator errors because of the reduction in human involvement.

One class of systems includes microfluidic "chips" that include very small fluid channels and small reaction/analysis chambers. These systems can be used for analyzing very small amounts of samples and reagents and can control liquid and gas samples on a small scale. Microfluidic chips have found use in both research and production, and are currently used for applications such as genetic analysis, chemical diagnostics, drug screening, and environmental monitoring. Although these systems may allow manipulation of small volumes of fluids, additional methods that allow further control and flexibility are needed.

Background art includes U.S. Pat. Nos. 8,592,221, 8,449,837 and International Patent Application WO2008/090557, international Patent Application WO/2015/052717; Nakano, A. & Ros, A. Electrophoresis 34, 1085-1096 (2013); Tuukkanen, S. et al. Nanotechnology 18, 295204 (2007); 20; and Hölzel, R., et al., Phys. Rev. Lett. 95, 128102 (2005).

SUMMARY OF THE INVENTION

According to an aspect of the present invention there is provided a method of controlling a biological process in a test chamber, wherein a portion of a surface of the test chamber is attached to at least one immobilized component of the biological process, the method comprising:

(a) providing non-immobilized components of the biological process to the test chamber under conditions that allow the non-immobilized components to react with the at least one immobilized component and carry out the biological process; and (b) applying an electric field gradient in the test chamber at a frequency which draws at least one non-immobilized component of the biological process away from the at least one immobilized component towards the source of the electric field gradient, thereby controlling the biological process.

According to an aspect of the present invention there is provided a method of controlling a biological process in a test chamber of a microfluidic device, wherein a surface of the test chamber is attached to at least one immobilized component of the biological process, the method comprising:

(a) providing non-immobilized components of the biological process to the microfluidic device under conditions that allow the non-immobilized components to reach the test chamber and carry out the biological process; and (b) applying an electric field gradient in the vicinity of the test chamber at a frequency which draws at least one non-immobilized component of the biological process away from the at least one immobilized component towards the source of the electric field gradient, thereby controlling the biological process.

According to an aspect of the present invention there is provided a microfluidic device comprising:

(i) at least one reaction unit having a test chamber connected to at least one microchannel, wherein a surface of at least a portion of the test chamber is attached to a component of a biological process;

(ii) a flow-through channel having at least one inlet port and at least one outlet port, the flow-through channel being connected to the reaction unit via the at least one microchannel;

(iii) a stimulation chamber which is connected to the test chamber; and (iv) two electrodes patterned into the device being in physical contact with the stimulation chamber, the two electrodes being at least 1-50 μm from the test chamber.

According to an aspect of the present invention there is provided a method of controlling a biological process in a test chamber of the microfluidic device described herein, the method comprising:

(a) providing non-immobilized components of the biological process to the microfluidic device under conditions that allow the non-immobilized components to reach the test chamber: and (b) applying an electric field gradient in the vicinity of the test chamber at a frequency which draws at least one non-immobilized component of the biological process away from the biomolecule towards the source of the electric field gradient, thereby controlling the biological process.

According to some embodiments of the invention, the biological process is DNA transcription, gene expression or protein modification.

According to some embodiments of the invention, the immobilized component of the biological process is a nucleic acid.

According to some embodiments of the invention, the applying the electric field gradient is effected between 0.01 second and 1 hour.

According to some embodiments of the invention, the method further comprises terminating the electric field gradient.

According to some embodiments of the invention, the frequency is between 0.1-10 MHz.

According to some embodiments of the invention, the electric field gradient is generated using an AC electric potential of at least 1 V.

According to some embodiments of the invention, the sequence of the nucleic acid encodes a promoter operatively linked to a nucleic acid sequence encoding a polypeptide.

According to some embodiments of the invention, the polypeptide is a detectable polypeptide.

According to some embodiments of the invention, the biological process is DNA transcription, gene expression or protein modification.

According to some embodiments of the invention, the immobilized component of the biological process is a nucleic acid.

According to some embodiments of the invention, the applying the electric field gradient is effected between 0.01 second and 1 hour.

According to some embodiments of the invention, the method further comprises terminating the electric field gradient.

According to some embodiments of the invention, the frequency is between 0.1-10 MHz.

According to some embodiments of the invention, the electric field gradient is generated using an AC electric potential of at least 1 V.

According to some embodiments of the invention, the maximal field intensity of the electric field gradient is localized at least 1-50 μm from the test chamber.

According to some embodiments of the invention, the at least two electrodes are patterned into the microfluidic device.

According to some embodiments of the invention, the at least two electrodes are patterned at least 1-50 μm from the test chamber.

According to some embodiments of the invention, the sequence of the nucleic acid encodes a promoter operatively linked to a nucleic acid sequence encoding a polypeptide.

According to some embodiments of the invention, the polypeptide is a detectable polypeptide.

According to some embodiments of the invention, the flow-through channel and the microchannel are of dimensions so as to allow diffusion through the microchannel with essentially no fluid flow through the microchannel.

According to some embodiments of the invention, the component is a nucleic acid.

According to some embodiments of the invention, the electrodes are between 0.1-20 μm in width.

According to some embodiments of the invention, the electrodes are between 0.1-30 μm apart.

According to some embodiments of the invention, the width ratio of the microchannel:flow-through channel is greater than 1:5.

According to some embodiments of the invention, the fluid flow resistance is higher in the reaction unit than in the flow-through channel.

According to some embodiments of the invention, the microfluidic device further comprises at least one valve to control flow of fluid through the flow-through channel.

According to some embodiments of the invention, the microfluidic device comprises at least two test chambers.

According to some embodiments of the invention, the test chamber is 10-200 microns in diameter.

According to some embodiments of the invention, the microfluidic device further comprises at least one external reservoir being in fluid communication with the inlet port.

According to some embodiments of the invention, the microfluidic device is fabricated from a substrate having attached thereto a plurality of monolayers the monolayers being composed of a compound which comprises a general formula I:

$$X-L-Y \qquad \text{Formula I}$$

wherein:

X is a functionalized group capable of binding to the substrate;

L is a polymer capable of forming the monolayer onto the substrate; and

Y is a photoactivatable group capable of generating a reactive group upon exposure to the light.

According to some embodiments of the invention, the nucleic acid is attached to the surface via a reactive group.

According to some embodiments of the invention, the reactive group is photoreactivatable.

According to some embodiments of the invention, the photoreactivatable reactive group is selected from the group consisting of amine, hydroxy, thiohydroxy, halo, alkoxy, thioalkoxy, aryloxy, thioaryloxy, carboxylate, phosphate, phosphonate, sulfate and sulfonate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

General Terminology

As used herein, the term "amine" describes both a —NR'R" group and a —NR'— group, wherein R' and R" are each independently hydrogen, alkyl, cycloalkyl, aryl, as these terms are defined herein.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, connecting another moiety at each end thereof.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The alkyl group can be an end group, as this term is defined hereinabove, wherein it is attached to a single adjacent atom, or a linking group, as this term is defined hereinabove, connecting two or more moieties at two or more positions thereof.

The term "halide" or "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, or an —O—S(=O)$_2$—O— linking group, as these phrases are defined hereinabove, where R' is as defined hereinabove. This term further encompasses thiosulfates.

The term "thiosulfate" describes a —O—S(=S)(=O)—OR' end group or a —O—S(=S)(=O)—O— linking group, as these phrases are defined hereinabove, where R' is as defined hereinabove.

The term "sulfonate" describes a —S(=O)$_2$—R' end group or an —S(=O)$_2$-linking group, as these phrases are defined hereinabove, where R' is as defined herein.

The term "sulfonamide" describes a —S(=O)$_2$—NR'R" end group or a —S(=O)$_2$—NR'— linking group, as these phrases are defined hereinabove, with R' and R" as defined herein. This term encompasses the terms N-sulfonamide and S-sulfonamide.

The term "N-sulfonamide" describes an R'S(=O)$_2$—NR"— end group or a —S(=O)$_2$—NR'— linking group, as these phrases are defined hereinabove, where R' and R" are as defined herein.

The term "S-sulfonamide" describes an —S(=O)$_2$—NR'R"— end group or a —S(=O)$_2$—NR'— linking group, as these phrases are defined hereinabove, where R' and R" are as defined herein.

The term "phosphonate" describes a —P(=O)(OR')(OR") end group or a —P(=O)(OR')(O)— linking group, as these phrases are defined hereinabove, with R' and R" as defined herein.

The term "phosphate" describes an —O—P(=O)$_2$(OR') end group or a —O—P(=O)$_2$(O)— linking group, as these phrases are defined hereinabove, with R' as defined herein. This term further encompasses the term thiophosphonate.

The term "thiophosphate" describes an —O—P(=O)(=S)(OR') end group or a —O—P(=O)(=S)(O)— linking group, as these phrases are defined hereinabove, with R' as defined herein.

The term "carbonyl" or "carbonylate" as used herein, describes a —C(=O)—R' end group or a —C(=O)— linking group, as these phrases are defined hereinabove, with R' as defined herein. Alternatively, R' can be halide, or any other reactive derivative. This term encompasses the term "thiocarbonyl".

The term "thiocarbonyl" as used herein, describes a —C(=S)—R' end group or a —C(=S)— linking group, as these phrases are defined hereinabove, with R' as defined herein.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "azo" describes an —N=NR' end group or an —N=N— linking group, as these phrases are defined hereinabove, with R' as defined hereinabove.

The term "carboxylate" describes a —C(=O)—OR' end group or a —C(=O)—O— linking group, as these phrases are defined hereinabove, where R' is as defined herein. This term encompasses the terms O-carboxylate, C-thiocarboxylate, and O-thiocarboxylate, as well as various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters.

The term "carbamate" describes an R"OC(=O)—NR'— end group or a —OC(=O)—NR'— linking group, as these phrases are defined hereinabove, with R' and R" as defined herein. This term encompasses the terms O-carbamate, thiocarbamate and include various derivatives thereof including, but not limited to, N— hydroxysuccinimide esters, N-hydroxybenztriazole esters, acid halides, acyl imidazoles, thioesters, p-nitrophenyl esters, alkyl, alkenyl, alkynyl and aromatic esters.

The term "amide" describes a —C(=O)—NR'R" end group or a —C(=O)—NR'— linking group, as these phrases are defined hereinabove, where R' and R" are as defined herein. This term encompasses the term N-amide.

The term "N-amide" describes a R'C(=O)—NR"— end group or a R'C(=O)—N—linking group, as these phrases are defined hereinabove, where R' and R" are as defined herein.

The term "hydrazine" describes a —NR'—NR"R'" end group or a —NR'—NR"— linking group, as these phrases are defined hereinabove, with R', R", and R'" as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "ester" describes a moiety containing a carboxylate group, as defined herein.

An "alkenyl" group describes an alkyl group which consists of at least two carbon atoms and at least one carbon-carbon double bond.

An "alkynyl" group describes an alkyl group which consists of at least two carbon atoms and at least one carbon-carbon triple bond.

A "dienophile" group describes a group which comprises at least two conjugated double-double boned.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 3A:
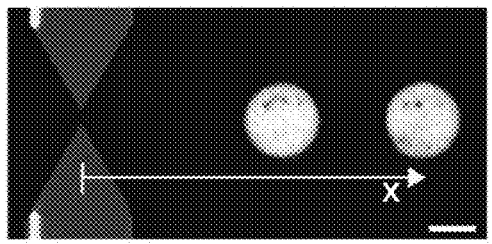

FIGS. 1A-E. Electric-field manipulation of gene expression in a DNA compartment. (A) (Left, E-field OFF): Image of expressed GFP overlaid with fluorescently labeled DNA coding for GFP under T7 promoter (squares, end-labeled by red fluorophore, 647 nm). Only one compartment was connected to gold electrodes (yellow). (Right, E-field ON): same imaging upon application of E-field to electrodes at 1 MHz, $10V_{pp}$. Scale bar: 100 μm. (B) Periodic pulses of protein synthesis driven by E-field for a duration of 5 min each, with third pulse at 10 MHz, $10V_{pp}$; E-field ON (green marks), E-field OFF (red marks). (C) Scheme: attraction of biomolecules to electrodes depletes RNAPs and ribosomes from DNA brush and inhibits gene expression. (D) Decay of GFP expression measured in DNA compartments as a function of distance from electrodes. (E) Numerical solution of kinetics of gene expression reaction in the compartment taking into account depletion of both RNAP and ribosomes (Eqs. S1-4).

FIGS. 2A-E. TIRFM Measurement of biomolecular trapping near electrodes. (A) Scheme: gold electrodes patterned on fused silica cover slip (100 nm, yellow) embedded in a circular PDMS chamber (250 μm thickness, 3 mm diameter), and mounted on a prism for detection of biomolecular localization close to the surface (~100 nm) by TIRF using a 488 nm continuous laser. Inset: side view. (B) Streamline imaging of fluorescently labeled latex beads (1 μm) moving under E-field (1 MHz, $10V_{pp}$) in distilled water. Images represent three consecutive frames (denoted by different colors) superposed and background subtracted to report change in time (FIGS. 7A-D). Scale bar 100 μm (C) TIRFM images of kinetics (time in sec as denoted) of ribosome-GFP attracted and adsorbed at region near electrodes by E-field (1 MHz, $10V_{pp}$). Scale bar 50 μm. (D) Measurement of trapping rate in GFP signal (arbitrary units) as a function of applied voltage; arrows denote threshold values, $V_{th}$, for GFP, ribosome-GFP, and RNAP-GFP, all at equal bulk concentration. (E) Trapping rate as a function of $V_{th}^2$ at applied voltage of $10V_{pp}$ (1 MHz).

FIGS. 3A-F. Depletion of biomolecules from DNA brushes undergoing gene expression on the surface. (A) TIRFM Image of DNA (end-labeled in red, 647 nm) patterned along x-axis from electrodes. Scale bar 50 μm. (B) Imaging transcription-translation activity at DNA brush in separate experiments. Labeled biomolecules before/after E-field (1 MHz, $10V_{pp}$) application: DNA, RNAP-GFP, nascent RNA (labeled by broccoli aptamer), and ribosome-GFP; scale bar 50 μm (C) Localization kinetics at DNA brush of RNAP-GFP, synthesized RNA, and ribosome-GFP in response to E-field (turned ON in yellow). Data given in fluoresce fold, $$\Delta F = \frac{F_{coding}}{F_{non\text{-}coding}}$$

of coding to non-coding DNA brushes patterned for reference on opposite side of electrodes (-x). (D) Recovery time of RNAP-GFP, nascent RNA and Ribosome-GFP after E-field was turned off, extracted as exponential fits to data (dashed line) in (C). (E) Decay in signal of localized ribosome-GFP after application of E-field, as a function of the distance from the electrodes. (F) Depletion time of ribosome-GFP localized to DNA brush during applied E-field as a function of the distance from the electrodes, extracted by exponential fits to data (C).

Figure 4:
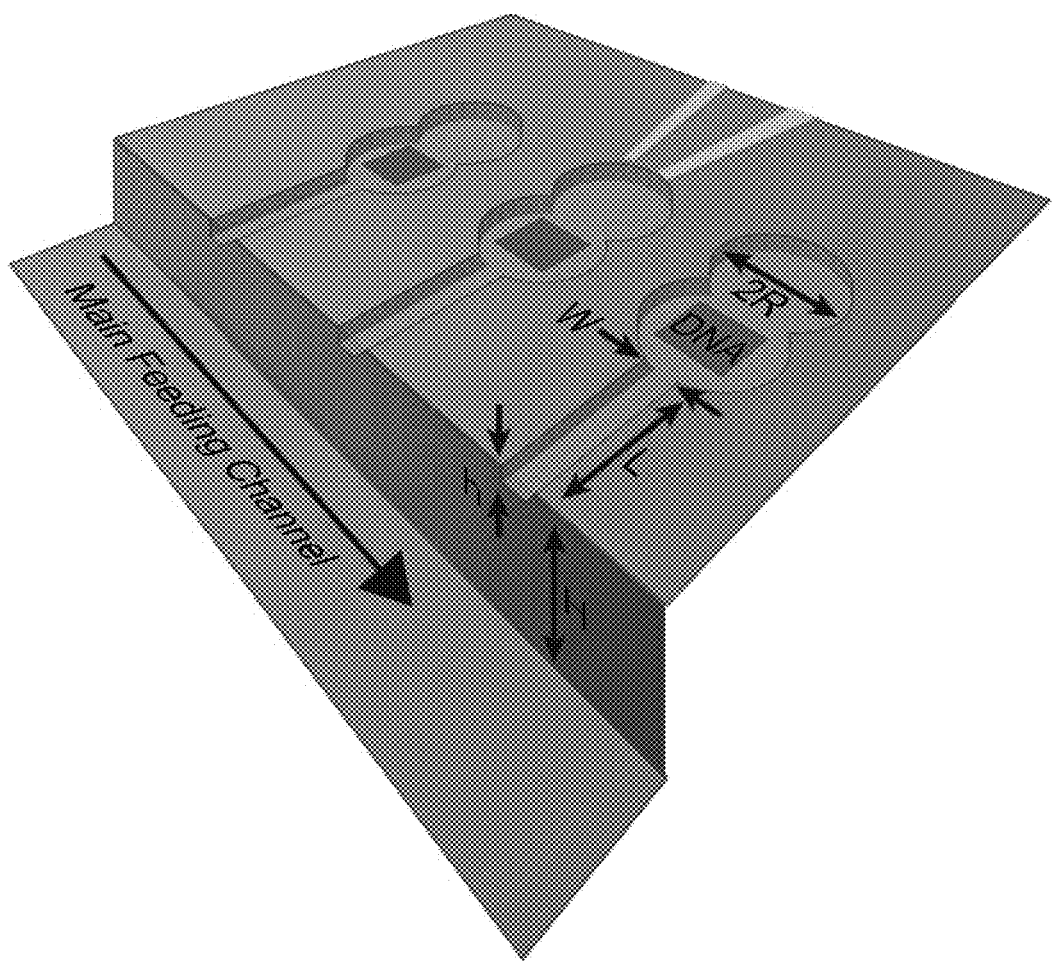

FIG. 4. Microfluidic chip illustration. DNA compartments were carved in silicon to a depth of h=3 μm, a radius of R=35 μm, with a capillary width of W=15 μm, and L=200 μm. Rectangular DNA brushes were patterned at the center of the bottom compartments. Gold electrodes were evaporated on the top substrate, reaching the top compartment (100 nm thin, distance between tips 25 μm). The main feeding channel was H=30 μm deep and 200 μm wide. The main feeding channel is filled with a PURE cell free expression reaction flowing at a constant flow of 0.4 μl/min.

FIGS. 5A-F. Numerical solution of DEP in DNA compartment. Gene expression dynamics of mRNA and proteins (eq 1-4) manipulated by depletion of machinery by E-field: (a) RNAP and Ribosome. (b) RNAP. (c) Ribosome. (d) mRNA. (e) GFP. (f) RNAP, mRNA, Ribosomes, and GFP.

Figure 6:
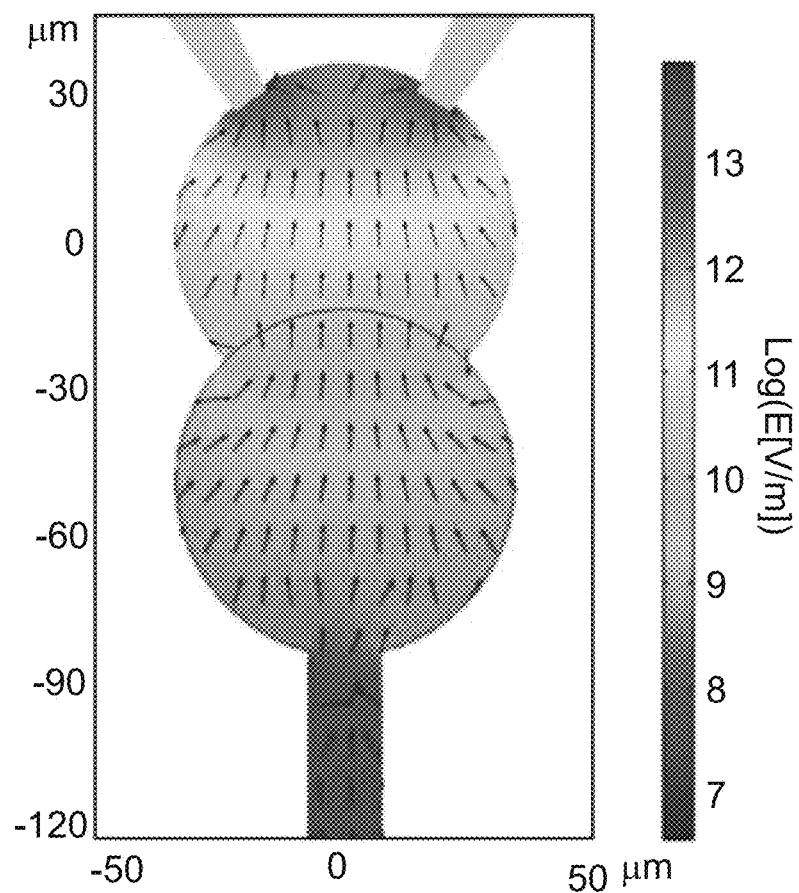
Figure 7:
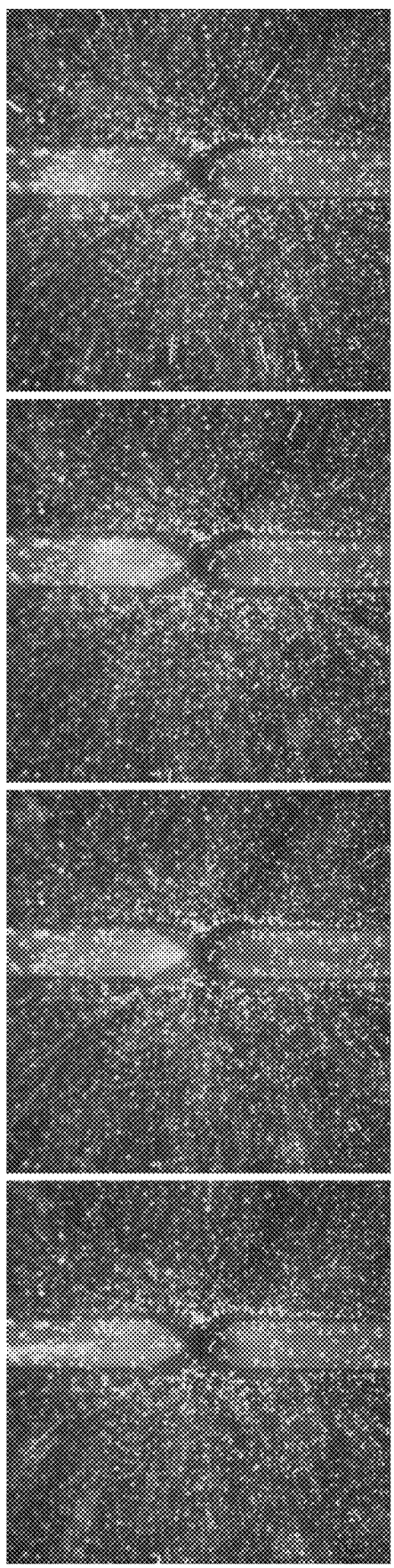

FIG. 6. Finite element simulations of DEP in the DNA compartment. Finite element numerical solution of the E-field spatial distribution (colored image), and DEP force directions $F \propto \nabla E^2$ (arrows represent direction but not magnitude of force.

FIGS. 7A-D. Raw images of E-field applied on beads. Image 2b created from an overlay image of (B)-(D) subtracted by (A) to remove absorption of beads.

Figure 8:
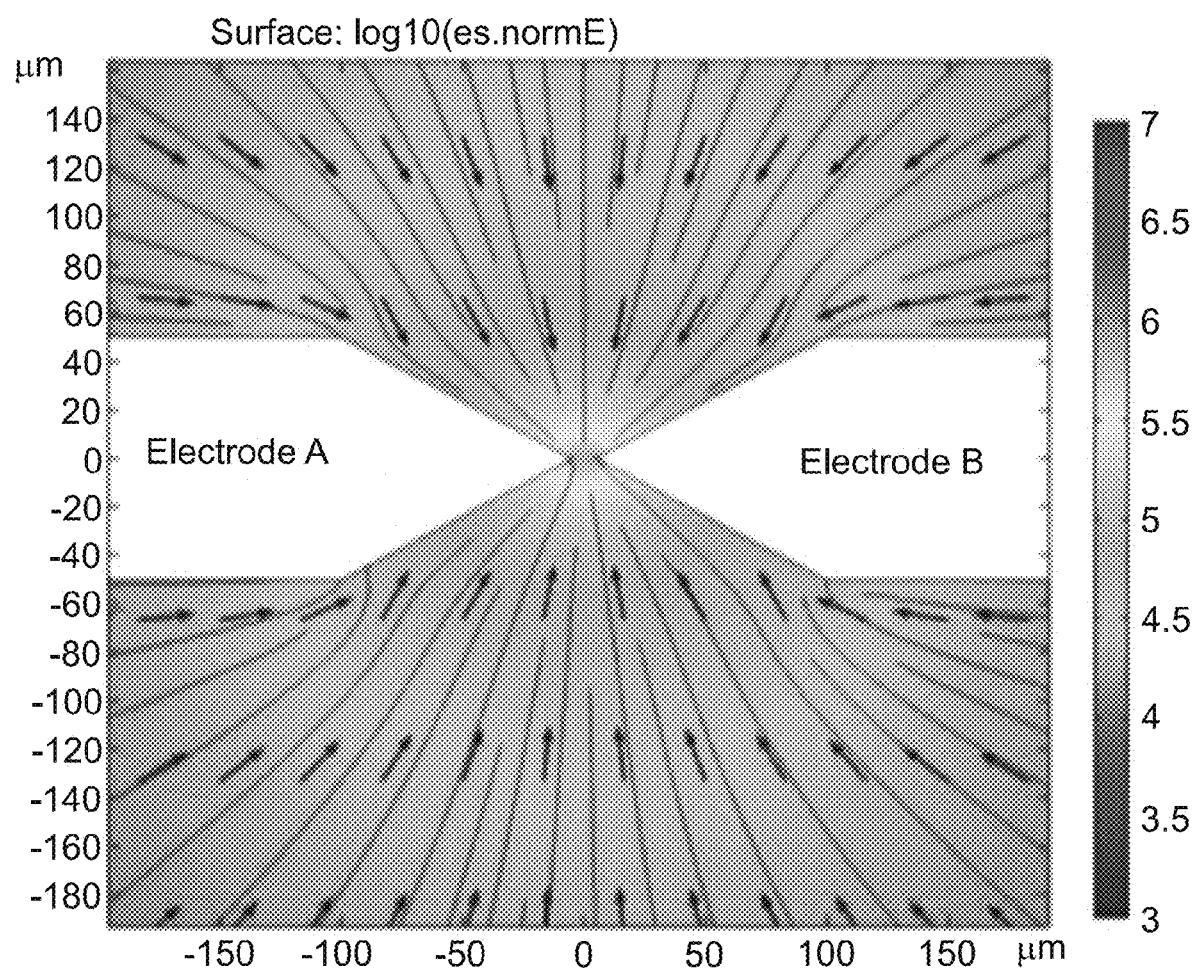

FIG. 8. Finite element simulations of DEP in PDMS well. Finite element numerical solution of the E-field spatial distribution (colored image), and DEP force directions $F \propto \nabla E^2$ (arrows represent direction but not magnitude of force).

Figure 9:
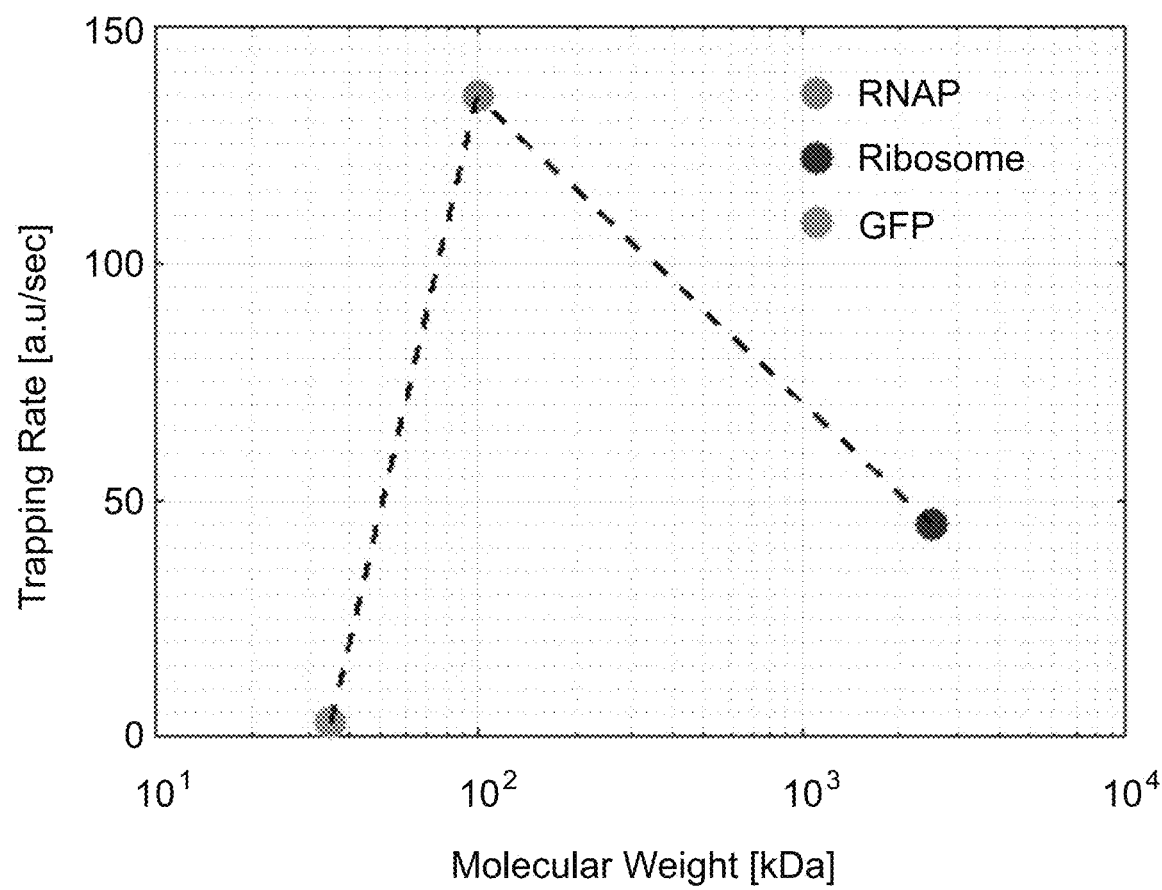

FIG. 9. Trapping rate of different biomolecules. Trapping rate of ribosome-GFP, RNAP-GFP, and GFP as a function of their molecular weight. Trapping rates were measured as the slope of the increased fluorescence between the electrodes upon application of E-field at 1 MHz $10V_{pp}$.

Figure 10:
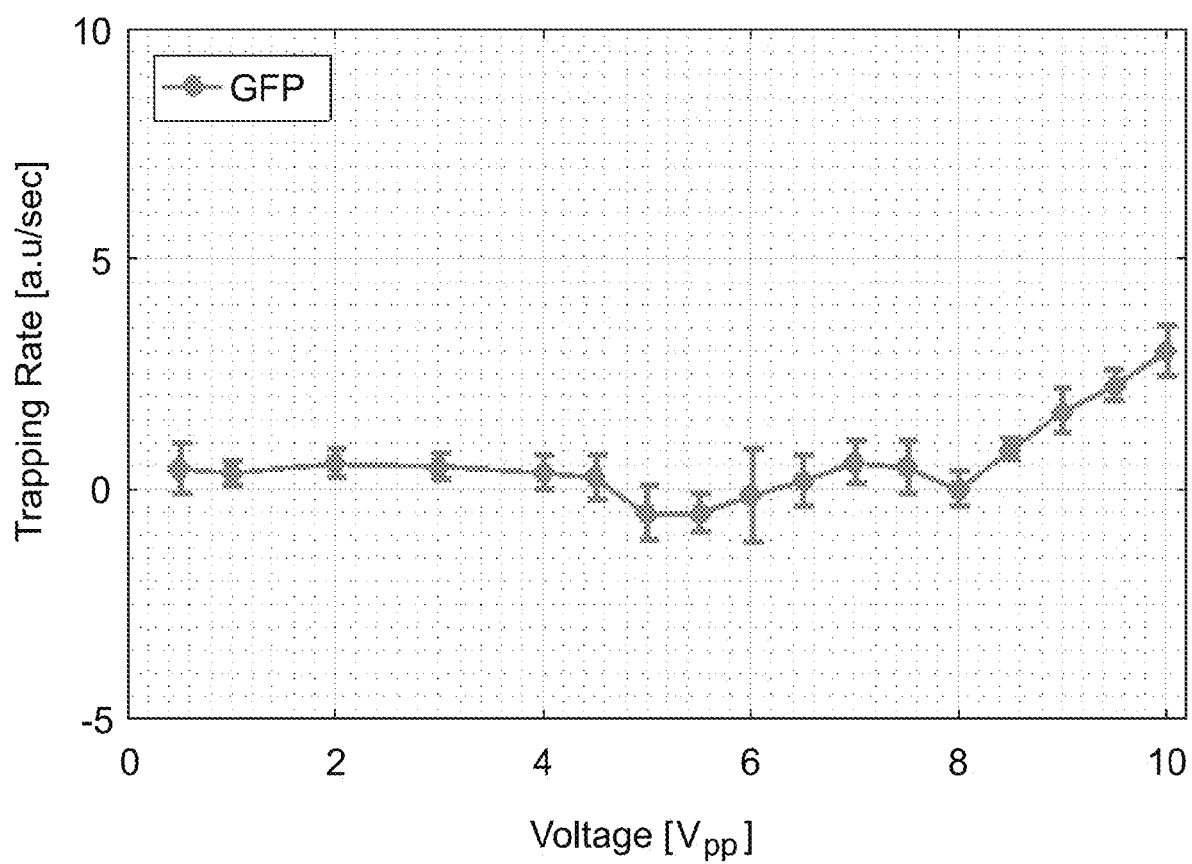

FIG. 10. Trapping rate of GFP. Zoom on data in FIG. 2D.

Figure 11:
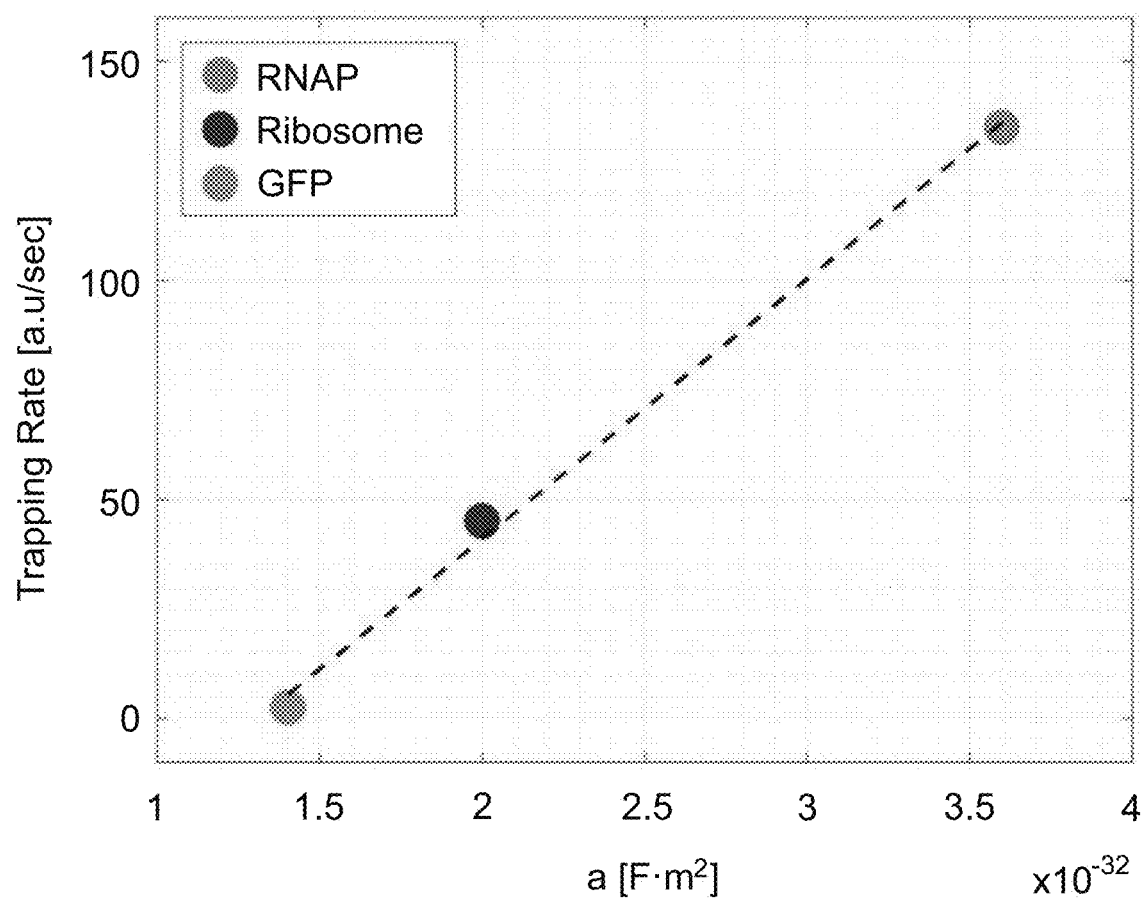

FIG. 11. Trapping rate as a function of molecule polarizability. Induced polarizability of RNAP-GFP, ribosome-GFP, and GFP at 1 MHz, $10V_{pp}$ calculated from $V_{th}$ (FIGS. 2D, E).

Figure 12:
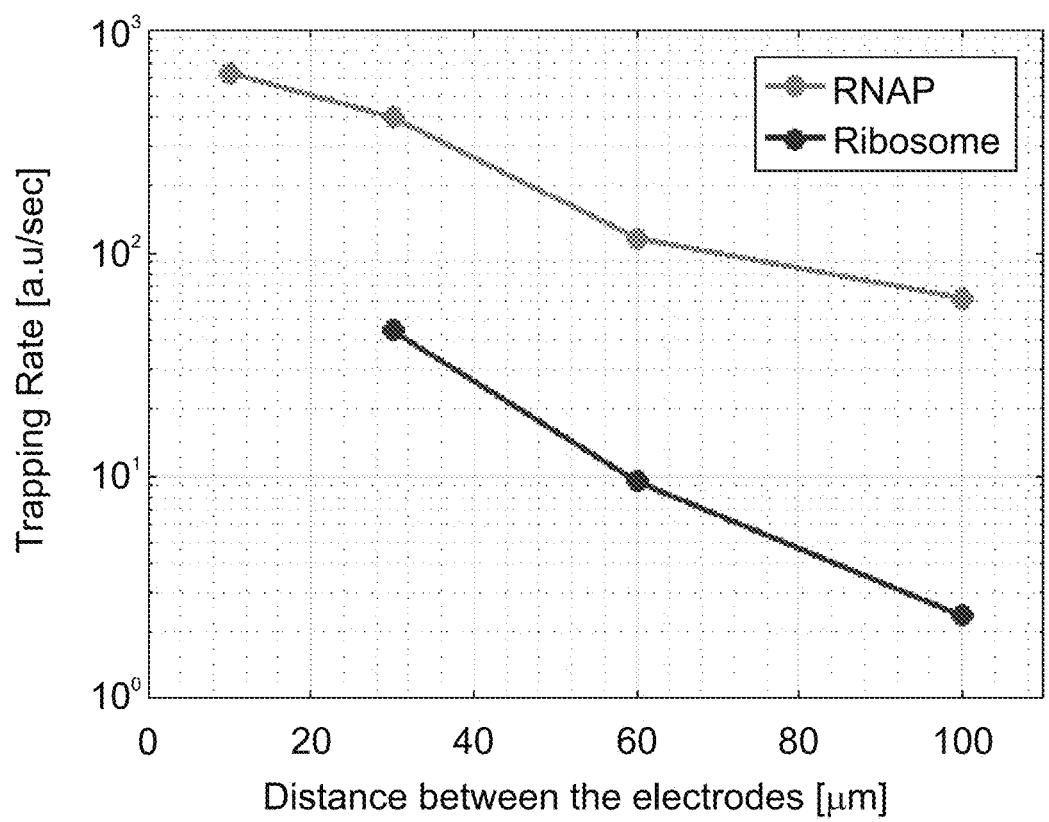

FIG. 12. Trapping rate of RNAP and ribosomes as a function of the distance between the electrodes. Trapping rate was measured for E-field application time shorter than 1 min, and calculated by:

$$\text{Trapping rate} = \frac{FL_{final} - FL_{initial}}{\text{interval}} \left[ \frac{a.u}{\sec} \right].$$

Figures 13A, 13B, 13C:
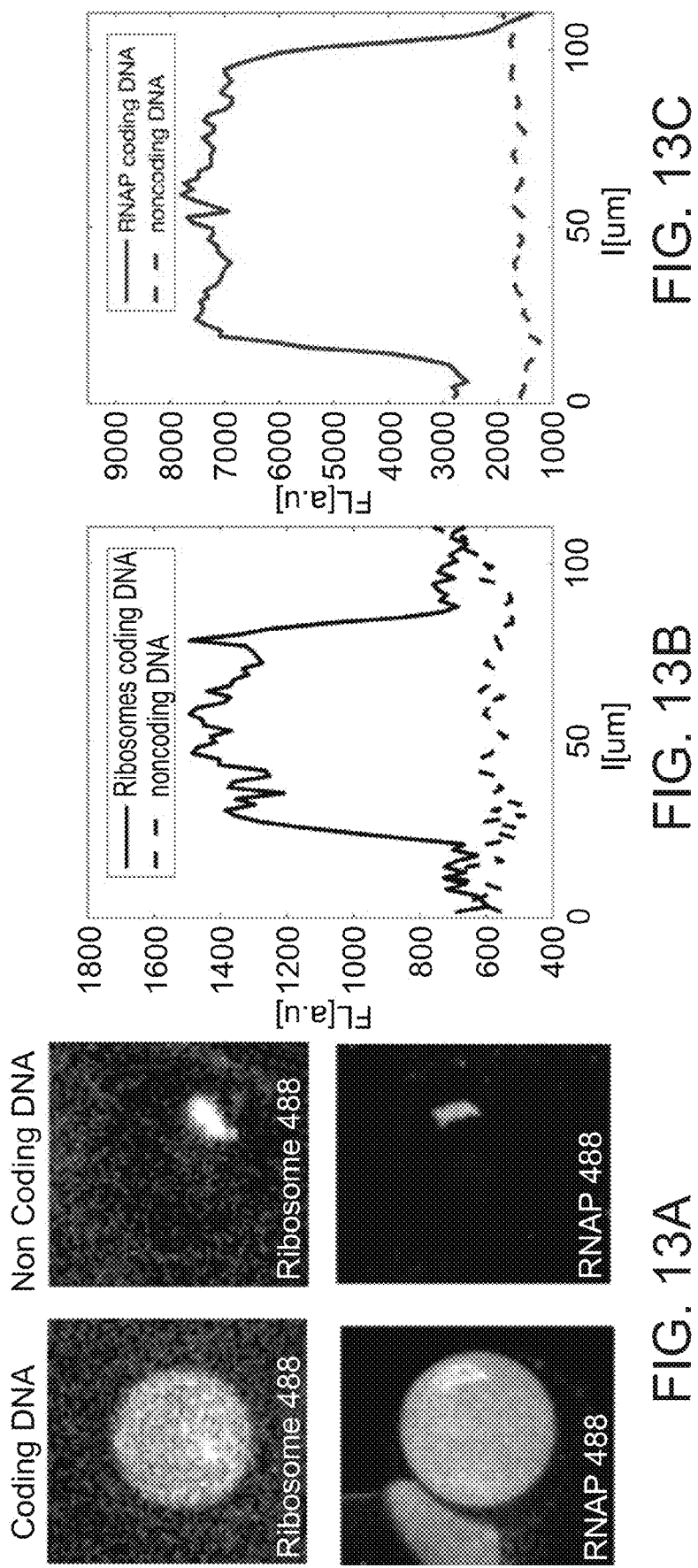
Figure 14A:
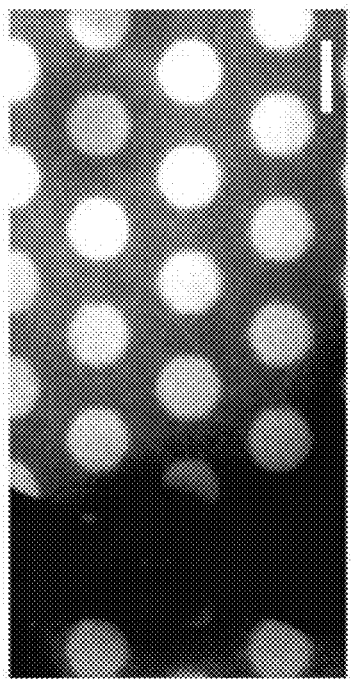
Figure 14B:
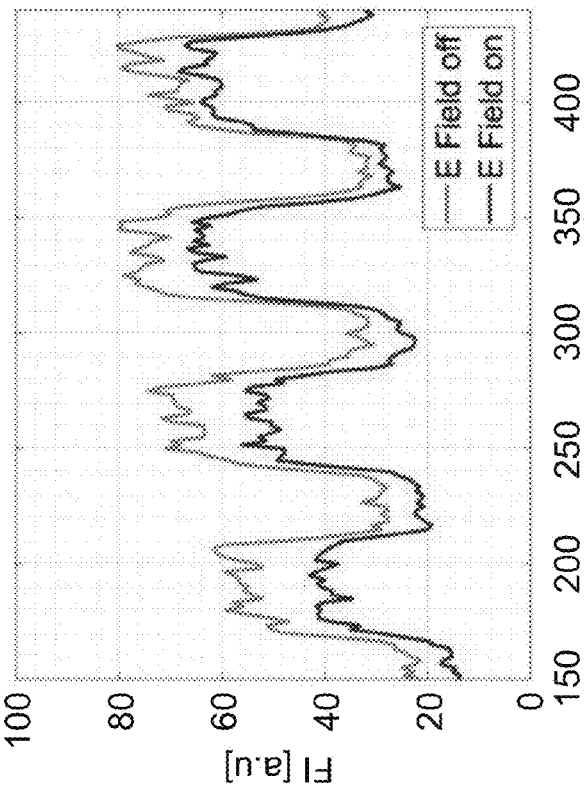
Figure 14C:
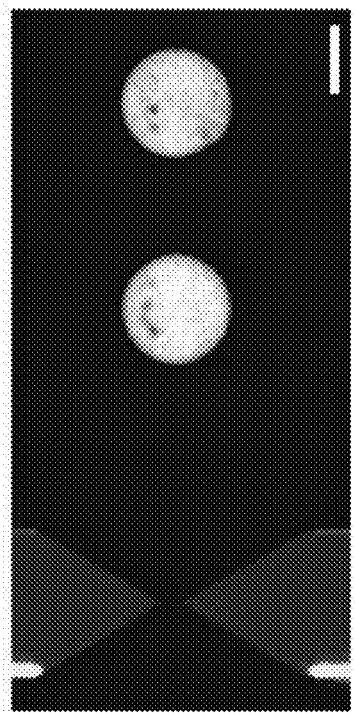
Figure 14D:
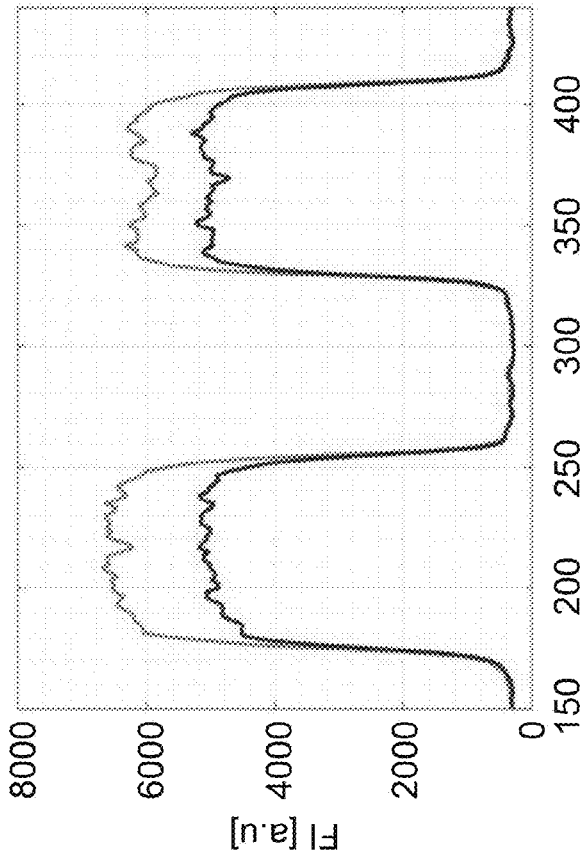

FIGS. 13A-C. Machinery localization. (A) TIRFM image of ribosome-GFP and RNAP-GFP localized to a coding DNA brush undergoing gene expression (left), and non-coding, inactive DNA brush (right). Fluorescent signals along the cross section of the brush for (B) ribosome-GFP, and (C) RNAP-GFP. Dashed lines are signals for noncoding DNA as background levels.

FIGS. 14A-D. Direct E-field effect on immobilized GFP. TIRFM images of (A) fluorescent DNA brush, and (B) localized GFP-HA attached to anti-HA antibodies patterned on the surface near the electrodes. Region within 100 μm of the electrodes was depleted of GFP-HA during initial immobilization step. Fluorescent profile of (C) DNA, and (D) GFP-HA as a function of the distance from the electrodes for E-field ON (red; $10V_{pp}$, 1 MHz) and OFF (blue).

Figure 15:
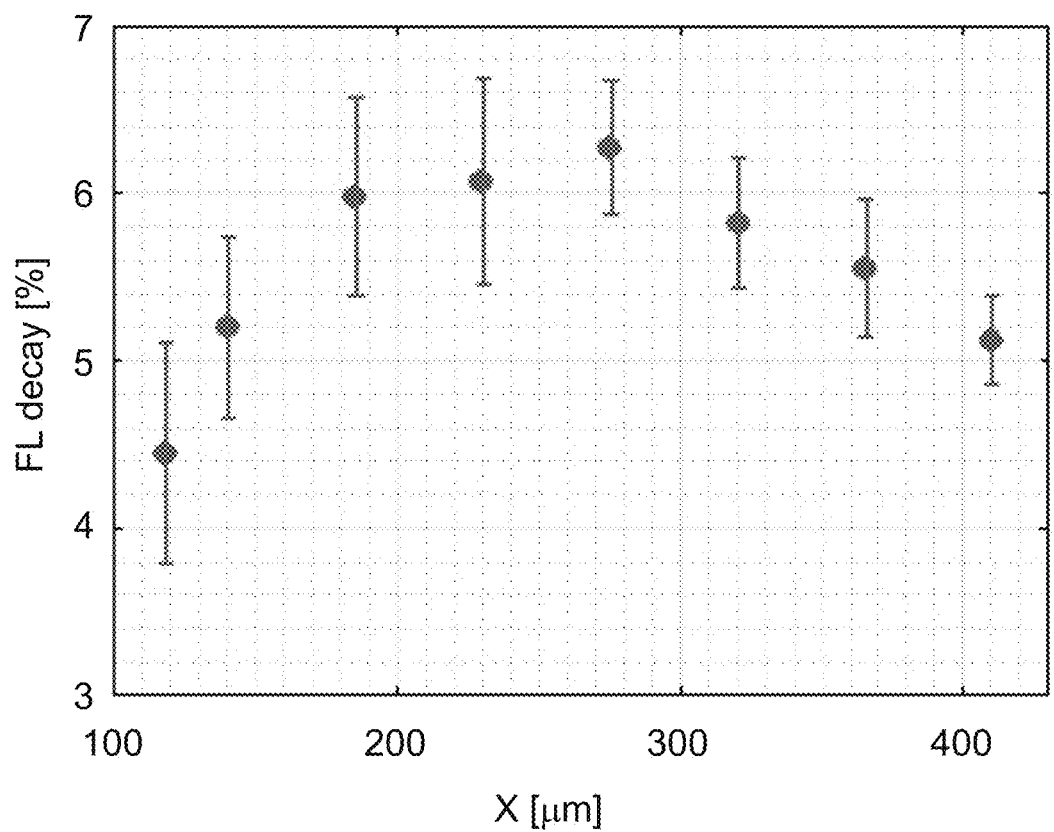

FIG. 15. Fluorescent decay of immobilized GFP as a function of the distance from the electrodes. Epi fluorescence measurement of Decrease in fluorescence of GFP-HA bound to the surface in a cell-free transcription translation reaction upon application of an E-field at 1M Hz, $10V_{pp}$.

Figure 16:
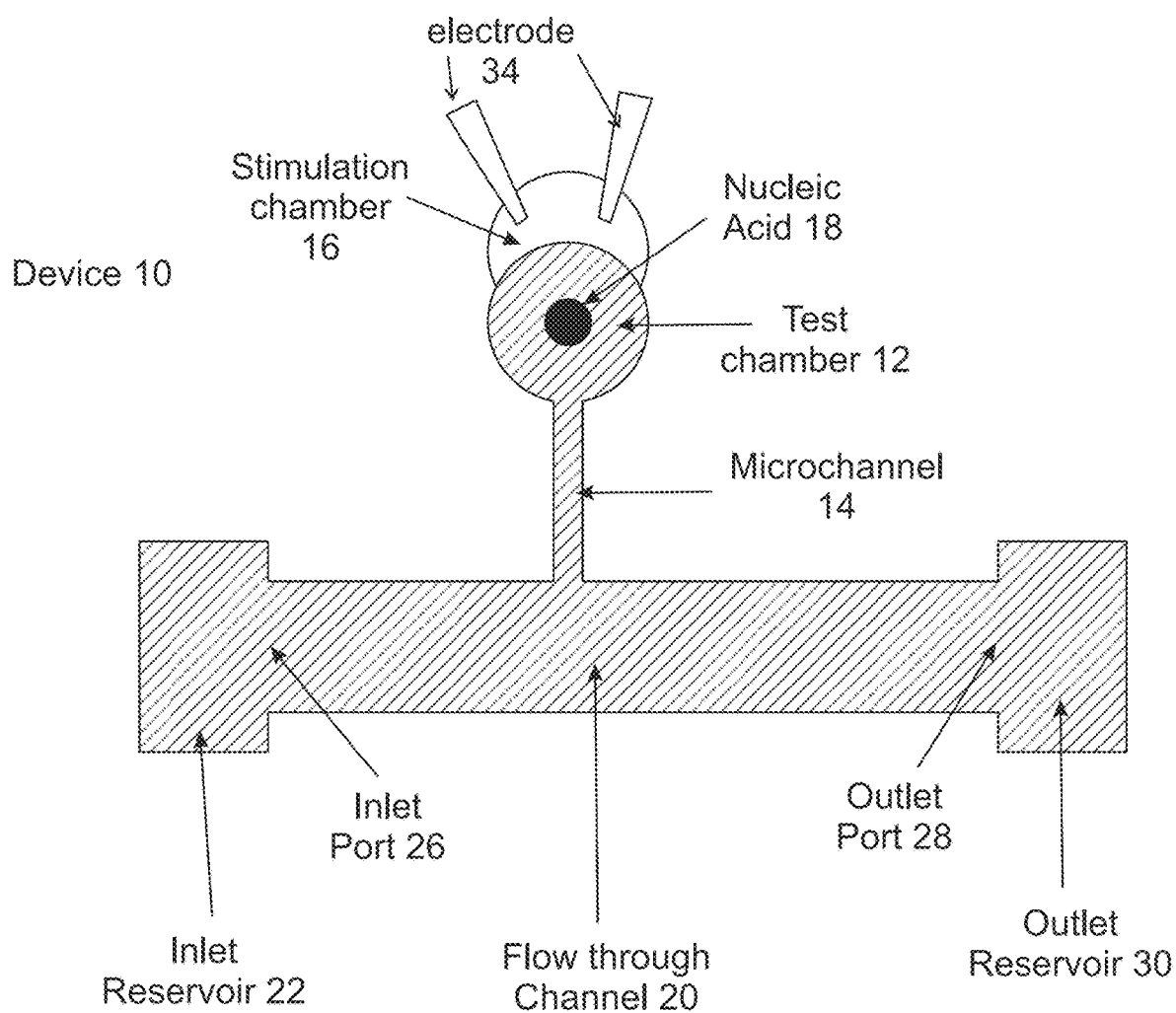

FIG. 16 is an illustration of a microfluidic device according to embodiments of the present invention.

Figure 17:
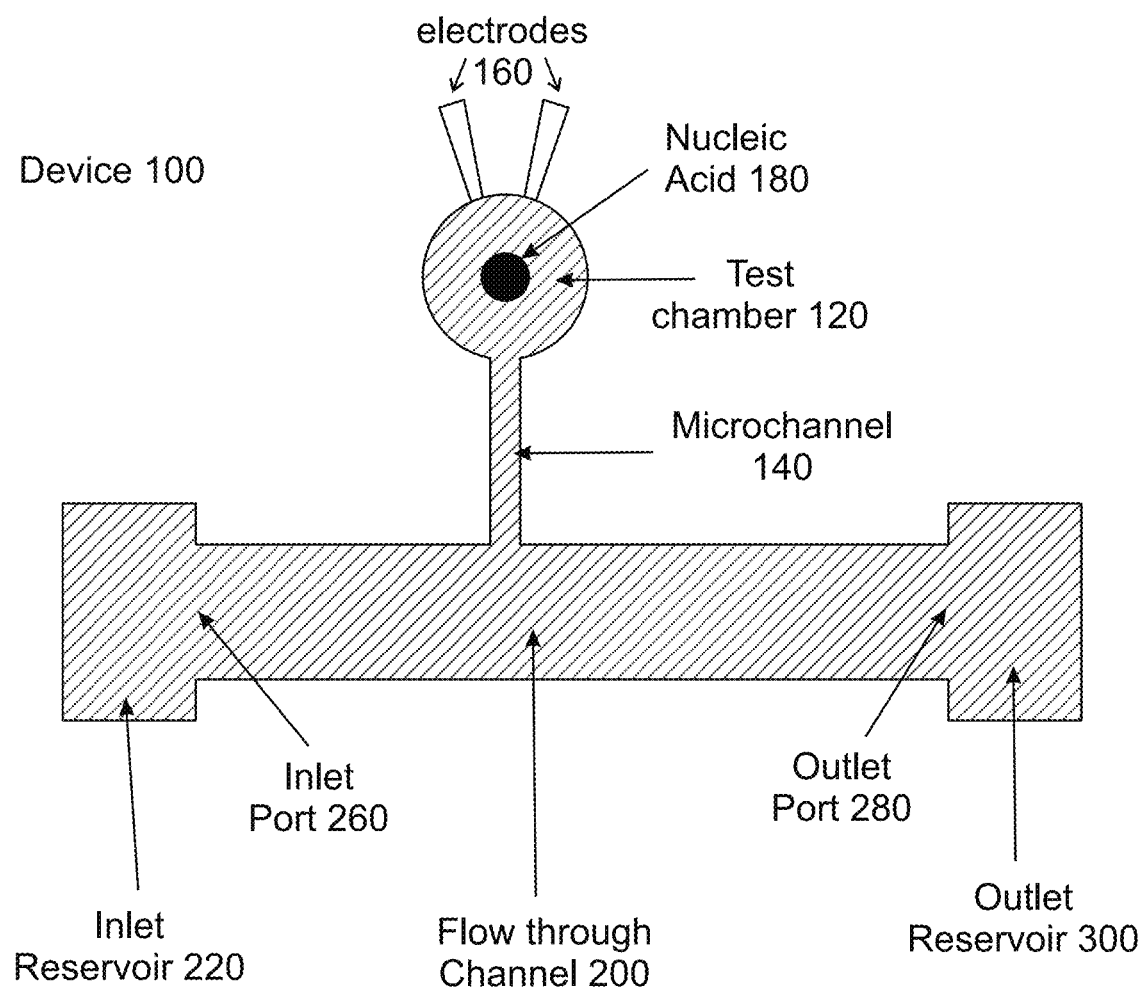

FIG. 17 is an illustration of a microfluidic device according to embodiments of the present invention.

Figure 18:
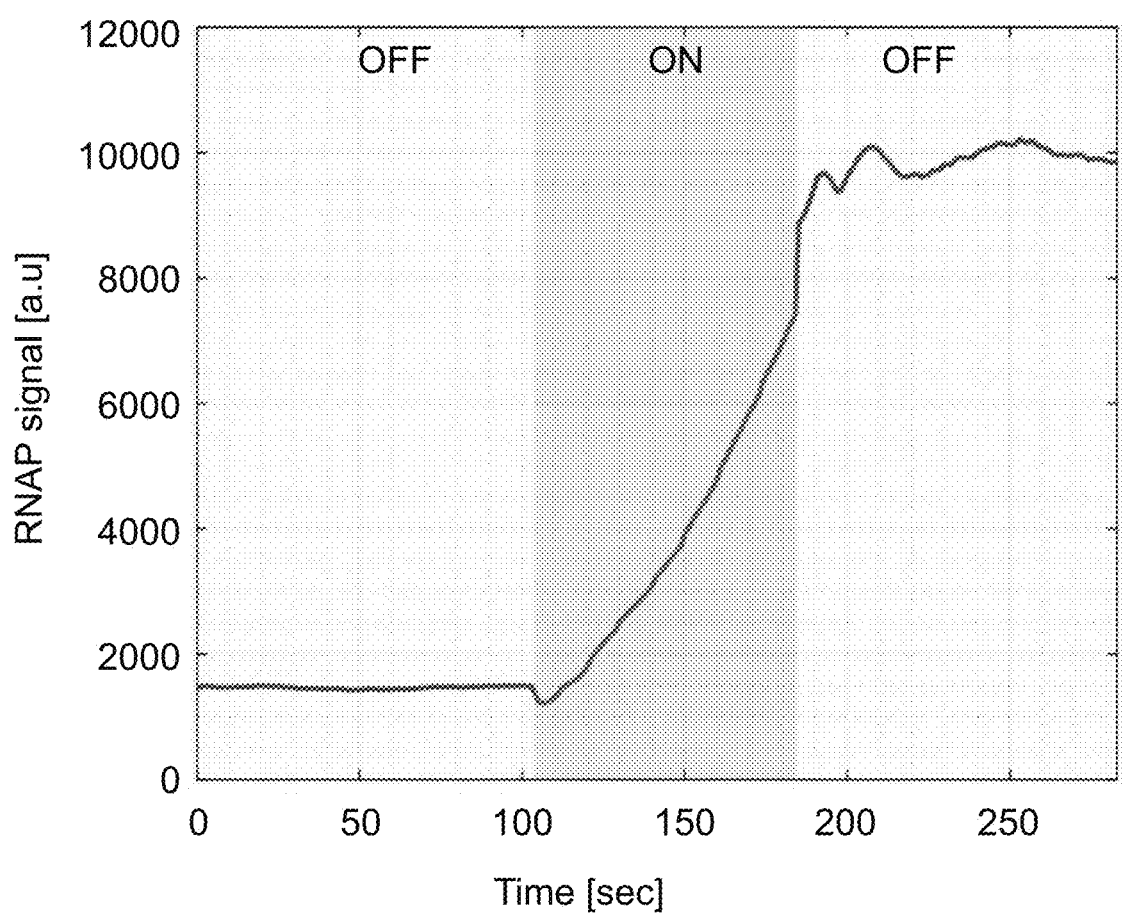

FIG. 18. RNAP-GFP Signal between the electrodes in response to E-field. RNAP-GFP signal was monitored by TIRF before, during (shaded area) and after and E-field pulse. The RNAP-GFP signal did not decrease subsequently, indicating adsorption of the protein to the surface.

DESCRIPTION OF SPECIFIC EMBODIMENTS OF THE INVENTION

The present invention, in some embodiments thereof, relates to use of electric field gradients to control biological reactions and, more particularly, but not exclusively, to control gene expression.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cellular complexity is governed by patterns of proteins that change in space and time. Recreating such patterns in a synthetic framework requires programming molecular interactions to regulate gene-expression reaction networks. The number of biological components that must be integrated scales up with the complexity of the network. The present inventors propose that synthetic biological design would be simplified if molecular regulation of gene expression were replaced by direct electric-field manipulation.

Whilst reducing the present invention to practice, the present inventors applied a localized electric field gradient at Mega-Hertz frequency to manipulate gene expression in a DNA compartment on a chip. The spatial symmetry of a homogenous reaction in the compartment was broken by creating a macromolecular trap in a region of maximal field intensity localized 50 microns from immobilized DNA. Free of biochemical regulation, the present inventors demonstrated protein synthesis oscillations by on/off switching of the electric field. In response to the field, ribosomes, RNA polymerases, and nascent RNA and proteins, accumulated in the trap, and were then depleted from the DNA region where gene expression occurred. The resulting reduction in the rate of protein synthesis recovered back to steady-state when the field was off. The combination of electric field with compartmentalized cell-free gene expression reactions creates a simple, label-free approach for controlling biomolecules in space and time, opening possibilities for hybrid biological systems with a bioelectronic interface based on minimal biological parts design.

Thus, according to an aspect of the present invention, there is provided a method of controlling a biological process in a test chamber, wherein a portion of a surface of the test chamber is attached to at least one immobilized component of the biological process, the method comprising:
  (a) providing non-immobilized components of the biological process to the test chamber under conditions that allow the non-immobilized components to react with the at least one immobilized component and carry out the biological process; and
  (b) applying an electric field gradient in the test chamber at a frequency which draws at least one non-immobilized component of the biological process away from the at least one immobilized component towards the source of the electric field gradient, thereby controlling the biological process.

The phrase "controlling a biological process" as used herein, refers to controlling the rate of a biological process. In one embodiment, the biological process is retarded. In another embodiment, the biological process is stopped. In another embodiment, the biological process is restarted.

Exemplary biological processes that may be controlled include, but are not limited to DNA transcription, RNA translation, DNA expression (i.e. transcription and translation) and protein modification.

The method of this aspect of the present invention is carried out in a test chamber, for example a test chamber of a microfluidic device, as further described herein below.

A "test chamber" as used herein, refers to an open or closed compartment in which the biological process (as described herein above) takes place. The test chamber may comprise volumes of between 10 pl-100 ml, more preferably between 10 pl-10 ml.

The test chamber may be any shape—e.g. rectangular, square or circular.

The test chamber or device of the present invention is fabricated from a substrate (i.e. a single material or a combination of materials).

Preferably, the substrate material is substantially non-fluorescent or emits light of a wavelength range that does not interfere with the photoactivation. Examples of such materials include, but are not limited to, silica-based materials (exemplified hereinbelow) and elastomeric materials.

The term "elastomer" and "elastomeric" as used herein refers to the general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application. Examples of elastomeric materials which can be used to fabricate the devices of the present invention include, but are not limited to, GE RTV 615 (formulation), a vinyl-silane crosslinked (type) silicone elastomer (family e.g., PDMS).

The choice of materials typically depends upon the particular material properties (e.g., solvent resistance, stiffness, gas permeability, and/or temperature stability) required for the application being conducted. Additional details regarding the type of materials that can be used in the manufacture of the components of the microfluidic devices disclosed herein are set forth in Unger et al. (2000) Science 288:113-116, and PCT Publications WO 02/43615, and WO 01/01025. Exemplary low-background substrates include those disclosed by Cassin et al., U.S. Pat. No. 5,910,287 and Pham et al., U.S. Pat. No. 6,063,338.

Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(l-butene), poly (chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In a preferred embodiment, the substrate material is substantially non-reactive with nucleic acids, thus preventing non-specific binding between the substrate and the nucleic acids. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

As mentioned the method of this aspect of the present invention may be carried out in a microfluidic device.

Thus, according to another aspect of the present invention there is provided a method of controlling a biological process in a test chamber of a microfluidic device, wherein at least one component of the biological process is immobilized to the surface of the test chamber, the method comprising:
  (a) providing non-immobilized components of the biological process to the microfluidic device under conditions that allow the non-immobilized components to reach the test chamber and carry out the biological process; and (b) applying an electric field gradient in the vicinity of the test chamber at a frequency which draws at least one of the non-immobilized components of the biological process away from the at least one component towards the source of the electric field gradient, thereby controlling the biological process.

As used herein the phrase "microfluidic device" refers to a synthetic device in which minute volumes of fluids are flowed. The flow-through channel of the device is generally fabricated at the micron to sub-micron scale, e.g., the flow-through channel typically has at least one cross-sectional dimension in the range of less than about 1 mm. Microfluidic devices of the present invention can be incorporated in complicated systems such as those described herein below.

The test chamber of a microfluidic device is connected to the flow-through channel such that components (i.e. non-immobilized components) which flow there-through can reach the test chamber and take part in the biological process (e.g. by diffusion or by fluid flow). In one embodiment, the flow-through channel is connected directly to the test chamber. In another embodiment, the flow-through channel is connected via a microchannel to the test chamber.

According to one embodiment, the test chamber of a microfluidic device is circular and has a diameter of about 50-200 microns. In a microfluidic device, the test chambers typically have a volume of less than 100 pl, in other instances less than 50 pl; in other instances less than 40 pl, 30 pl, 20 pl or 10 pl.

The term "flow-through channel" as used herein, refers to a low resistance flow channel, about 25 microns to about 150 microns deep, preferably about 25 microns to about 100 microns deep and more preferably about 30 microns to about 100 microns deep. Flow-through channels are sufficiently wide so as to not inhibit the flow of fluid through the channel, and not excessively wide to inhibit the function of valves. Such considerations are well understood by those of ordinary skill in the art. Exemplary widths of the flow-through channel are between 100 microns-1 mm wide. The flow-through channel has at least one inlet port and at least one outlet port, at least one of which being in fluid communication with a reservoir such as by tubing. Fluids may be passively or actively infused into the flow channels such as by capillary forces or pumps (e.g., external pumps, e.g., peristaltic pumps or electro-osmotically pumps).

Flow through the flow-through channel may be regulated using a valve.

A "valve" is a component of the device that regulates flow through a fluid channel of the device by substantially inhibiting flow through the fluid channel upon closure. Substantially inhibiting the flow means that flow is inhibited at least 80%, preferably at least 90%, more preferably at least 95%, even more preferably at least 99%, most preferably flow is completely (i.e., 100%) inhibited. The size of the valve is dependent on the size and shape of the fluid channel and the amount of pressure required to close the valve. In a preferred method, the fluid channel is about 250 microns wide and the valve is about 300 microns wide. The channel and control valve cross perpendicularly. Upon actuation of the valve, preferably by hydrostatic pressure, the channel closes and opens.

The term "microchannel" as used herein, refers to a high resistance channel, about 1 micron to about 20 microns deep, more preferably about 1 micron to about 10 microns deep. The length of the microchannel can vary between 20 microns to about 1 mm or between 20 microns to about 500 microns. The width of the microchannel is typically between 2-50 microns. According to embodiments of the present invention the ratio of the width of microchannel:width of the flow-through channel is greater than 1:5. Exemplary ratios include 1:5, 1:6, 1:7, 1:8, 1:9, 1:10 and 1:20.

According to a particular embodiment, the hydrodynamic resistance of the microchannel is at least 5 or 6 orders of magnitude higher than in the flow-through channel. This reduces the flow in the microchannel by 5 or 6 orders of magnitude compared with the flow in the flow chamber.

Resistance of fluid flow through the microchannel may be higher than the resistance in the flow-through channel. This resistance is typically established by having microchannels that are substantially and sufficiently shallower and/or narrower than the adjacent flow-through channels to create resistance. In one embodiment, the relative dimensions of the microchannel: flow-through channel is such that there is essentially no flow in the microchannel. Such parameters can be readily determined by one of ordinary skill in the art using mathematical or empirical modeling. According to a particular embodiment, the depth ratio of the reaction unit: flow-through channel is greater than 1:5. Exemplary ratios include 1:5, 1:6, 1:7, 1:8, 1:9, 1:10 and 1:20.

As mentioned, the surface of at least a portion of the test chamber is attached to at least one component of the biological process.

According to one embodiment, the at least one component is an isolated protein or peptide.

As used herein, the phrase "isolated protein or peptide" refers to a protein or peptide which is not comprised in or on a cell.

According to another embodiment, when the isolated protein or peptide is attached to the test chamber, it is devoid of cellular components (such as nucleic acids, lipids etc.)

According to another embodiment, the at least one component is an isolated nucleic acid.

As used herein, the phrase "isolated nucleic acid" refers to a nucleic acid which is not comprised in or on a cell.

According to another embodiment, when the isolated nucleic acid is attached to the reaction unit, it is devoid of cellular components (such as proteins, lipids etc.)

The nucleic acid may be single stranded or double stranded. The nucleic acid may be DNA (e.g. cDNA, genomic DNA, synthetic DNA), RNA, a combination of both. The nucleic acid may be isolated from a cell, or may by synthesized in vitro. Typically, the nucleic acids of this aspect of the present invention comprise at least one promoter and encode a polypeptide.

The nucleic acids may be of any length. According to a particular embodiment, the nucleic acids are between 200 bp-500 kbp, or between 200 bp-2000 kbp, or between 200 bp-100 kbp, or between 200 bp-40 kbp, or between 200-5000 bp.

According to a particular embodiment, the distance between the DNA top and the promoter is about 200 bp and a similar distance between the terminator and the DNA end attached to the surface.

Nucleic acids of this aspect of the present invention are further described herein below.

The nucleic acids and peptides of this aspect of the present invention are typically linear.

According to one embodiment, at least a portion of the surface of the test chamber (or portion thereof) is coated with the component (e.g. nucleic acids).

Preferably, the density of the nucleic acid on the surface of the test chamber is between $10^2$ DNA μm$^2$-$10^5$ DNA μm$^2$, for example in the order of $10^2$ DNA μm$^2$.

The nucleic acid of the present invention is typically orientated on the substrate of the test chamber such that the regulatory region of the nucleic acid (e.g. promoter) is closer to the substrate and the polypeptide coding region is further from the substrate.

The components (e.g. isolated nucleic acids) may be attached to the substrate of the test chamber (or portion thereof) in a wide variety of ways, as will be appreciated by those in the art. The components (e.g. nucleic acids) may either be synthesized first, with subsequent attachment to the substrate, or may be directly synthesized on the substrate of the test chamber. The test chamber and the component (e.g. nucleic acid) may be derivatized with chemical functional groups for subsequent attachment of the two. For example, the test chamber may be derivatized with a chemical functional group including, but not limited to, amino groups, carboxyl groups, oxo groups or thiol groups. Using these functional groups, the nucleic acid may be attached using functional groups on the nucleic acid either directly or indirectly using linkers.

The isolated nucleic acid may also be attached to the test chamber non-covalently. For example, a biotinylated nucleic acid can be prepared, which may bind to surfaces covalently coated with streptavidin, resulting in attachment. Alternatively, a nucleic acid may be synthesized on the surface using techniques such as photopolymerization and photolithography. Additional methods of attaching nucleic acids to solid surfaces and methods of synthesizing nucleic acids on solid surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

According to a preferred embodiment of this aspect of the present invention, the test chamber is coated with a coat composed of a compound which can be represented by the general formula I below:

X-L-Y            Formula I wherein X is the functionalized group capable of binding to a solid surface of the microfluidic device; L is the polymer capable of forming a monolayer on the microfluidic device; and Y is a photoactivatable group capable of generating a reactive group upon exposure to light.

The functionalized group is preferably selected such that it binds to the test chamber by reacting with at least one functional group present on a surface of the test chamber.

Preferred functionalized groups according to the present invention comprise one or more reactive silyl group(s).

As used herein, the phrase "reactive silyl group" describes a residue of a compound comprising at least one silicon atom and at least one reactive group, such as an alkoxy or halide, such that the silyl group is capable of reacting with a functional group, for example on a surface of the microfluidic device, to form a covalent bond with the surface. For example, the reactive silyl group can react with the surface of a silica substrate comprising surface Si—OH groups to create siloxane bonds between the compound and the silica substrate.

Exemplary reactive silyl groups that are usable in the context of the present invention include, without limitation, trialkoxysilanes, alkyldialkoxysilanes, alkoxydialkylsilanes, trihalosilanes, alkyldihalosilanes and dialkylhalosilanes.

Such reactive groups are easily reacted when contacted with free hydroxyl groups on a surface of solid surfaces and particularly with such hydroxyl groups on a silica surface.

Herein, the terms "silica" and "SiO$_2$" are used interchangeably.

In a preferred embodiment of the present invention the reactive silyl group is trialkoxysilane such as, for example trimethoxysilane, triethoxysilane, tripropyloxysilane or trihalosilane such as, for example, trichlorosilane.

The functionalized group according to the present invention may further include a chemical moiety that is terminated with the reactive silyl group. Such a chemical moiety can comprise, for example, alkyl, alkenyl, aryl, cycloalkyl and derivatives thereof, as these terms are defined herein.

Preferably, the functionalized group comprises an alkyl terminating with a trialkoxysilane.

As discussed hereinabove, the polymer is selected so as to form a monolayer on the test chamber. Thus, the polymer group in the compounds of the present invention may be any hydrophobic, hydrophilic and amphiphilic polymer that has suitable characteristics for forming a monolayer. Such characteristics include, for example, long, relatively inert chains, which may interact therebetween via e.g., hydrogen or Van-der-Waals interactions.

A preferred polymer according to the present invention comprises polyethylene glycol (PEG). As described hereinabove, PEG is characterized by resistance to nonspecific absorptions of biomolecules and is therefore beneficial for use in some contexts of the present invention. In addition, when self-assembled on a substrate, PEG chains typically interact therebetween via hydrogen bonds, so as to produce a well-ordered monolayered film.

The polyethylene glycol residue in the compounds of the present invention can be derived from PEGs having a molecular weight that ranges from about 400 grams/mol and about 10000 grams/mol. Preferred PEGs are those having a molecular weight that ranges from about 2000 grams/mol and about 5000 grams/mol. Such PEGs allow the productions of a monolayered film when deposited on a solid surface in the presence of a functionalized group, as described hereinabove.

The polyethylene glycol residue may be substituted or unsubstituted and can be represented by the general Formula II below:

—(CR$^1$R$^2$CR$^3$R$^4$O)n-            Formula II wherein n is an integer from 10 to 200; and R$^1$, R$^2$, R$^3$ and R$^4$ are each independently selected from the group consisting of hydrogen, alkyl, cycloalkyl, aryl, alkenyl alkynyl, alkoxy, thioalkoxy, aryloxy and thioaryloxy.

In a preferred embodiment, the PEG is unsubstituted such that R$^1$, R$^2$, R$^3$ and R$^4$ are each hydrogen.

In another preferred embodiment, the PEG residue is a medium-sized residue such that n is an integer from 60 to 100.

The polymer is preferably attached to the functionalized group described above via a linking moiety.

Exemplary linking moieties include, without limitation, oxygen, sulfur, amine, amide, carboxylate, carbamate, sulphonate, sulphonamide, phosphate, hydrazine, hydrazide, as these terms are defined herein and derivatives thereof.

In a representative example the linking moiety is an amide, formed between a carboxylic end group of the polymer and an amine end group of the functionalized moiety, as is detailed herein under.

The compounds of the present invention, by comprising the functionalized group and the polymer described hereinabove, readily form self-assembled monolayers when contacted with the solid surface of the test chamber, in a one-step, simple to perform, reaction.

As the polymer residue in the compounds of the present invention further has a photoactivatable group attached thereto, each of the formed monolayers has a photoactivatable group attached thereto.

As used herein, the phrase "photoactivatable group" describes a group that is rendered active when exposed to photoactivation, namely when exposed to light. Photoactivatable groups typically comprise a protected reactive group, which upon exposure to light are de-protected, so as to generate a reactive group.

As used herein, the phrase "reactive group" describes a chemical moiety that is capable of interacting with another moiety. This interaction typically results in a bond formation between these moieties, whereby the bond can be, for example a covalent bond, a hydrogen bond, a coordinative bond, or an ionic bond.

Representative examples of reactive groups include, without limitation, amine, hydroxy, thiohydroxy, halo, alkoxy, thioalkoxy, aryloxy, thioaryloxy, carboxylate, phosphate, phosphonate, sulfate and sulfonate, as these terms are defined herein.

Depending on the intended use of the compound, the photoactivatable group is selected so as to generate a desired reactive group Thus, for example, a photoactivatable group that comprises a carbamate can generate upon exposure to light amine as the reactive group.

The photoactivatable groups according to the present invention are preferably derived from photoactivatable compounds and therefore preferably include a residue of, for example, photoactivatable compounds that has light-absorbing characteristics such as 6-nitrovertaryl chloroformate, 6-nitrovertaryl carbonyl, 2-nitrotoluene, 2-nitroaniline, phenacyl, phenoxy, azidoaryl, sulfonic ester, desyl, p-hydroxyphenacyl, 7-methoxy coumarin, o-ethylacetophenone, 3,5-dimethylphenacyl, dimethyl dimethoxybenzyloxy carbonyl, 5-bromo-7-nitroindolinyl, o-hydroxy-α-methyl cinnamoyl and 2-oxymethylene anthraquinone.

When exposed to light such as, for example, UV, IR, or visible light or a monochromatic light of a predetermined wavelength, reactive groups, which are capable of nucleic acids, as is detailed hereinunder, are generated.

The above-described compounds can be readily prepared using a simple two-step synthesis. A process of preparing the compounds is described in details in PCT Application No. WO2006/064505 to the present inventor.

As discussed hereinabove, the surface of the test chamber and the compound of the present invention are selected such that upon contacting the polymer with the substrate, a self-assembled monolayered film of the polymer forms on the substrate surface, in a one-step reaction.

The contacting procedure is preferably effected by incubating the compound with the selected surface, preferably in the presence of an organic solvent such as, for example, toluene.

Once a monolayered film of the polymer is deposited on the surface, the reactive group for binding a screenable moiety can be generated by exposing a pre-selected area of the substrate to light.

Depending on the selected photoactivatable group and the active wavelength in which it is active, the light can be a UV, IR or visible light, or, optionally and preferably, the light can be a monochromatic light of a predetermined wavelength.

Exposure of a limited area of the test chamber surface to light is preferably effected using a photo mask to illuminate selected regions the substrate and avoid coating the substrate at the periphery. However, other techniques may also be used. For example, the solid surface may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the solid surface. Alternatively, synthesis may take place on the end of a series of optical fibers to which light is selectively applied. Other means of controlling the location of light exposure will be apparent to those of skill in the art.

The surface of the test chamber may be irradiated either in contact or not in contact with a solution and is, preferably, irradiated in contact with a solution. The solution may contain reagents to prevent the by-products formed by irradiation. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, or reducing agents (e.g., NADH).

In an exemplary embodiment, exposing the test chamber surface to light is effected so as to provide a patterned substrate in which reactive groups are generated according to a pre-selected pattern. The pattern can be printed directly onto the substrate or, alternatively, a "lift off" technique can be utilized. In the lift off technique, a patterned resist is laid onto the substrate or onto the light source. Resists are known to those of skill in the art. See, for example, Kleinfield et al., J. Neurosci. 8:4098-120 (1998). In some embodiments, following removal of the resist, a second pattern is printed onto the substrate on those areas initially covered by the resist; a process that can be repeated any selected number of times with different components to produce an array having a desired format.

Binding the nucleic acid can be effected by directly attaching the moiety to the reactive group.

Alternatively, binding the nucleic acid is effected via a mediating moiety. As used herein, the phrase "mediating moiety" describes a mediating agent or a plurality of mediating agents being linked therebetween that may bind to both the reactive group and the component and thus mediate the binding of the component to the reactive group.

The mediating moiety can thus be a bifunctional moiety, having two reactive groups, each independently capable of reacting with the reactive group attached to the test chamber or the component. Alternatively, the mediating moiety can comprise two or more moieties, whereby the first moiety can be attached to the reactive group and to a second mediating moiety, whereby the second mediating moiety can bind the component (e.g. nucleic acid).

Optionally and preferably, the mediating moiety comprises an affinity pair, such as, for example, the biotin-avidin affinity pair. The biotin-avidin affinity pair is highly useful for integrating nucleic acids or peptides on the surface of the test chamber.

Alternatively, the mediating moiety can comprise biotin. When attached to the reactive group, biotin can bind a variety of chemical and biological substances that are capable of reacting with the free carboxylic group thereof.

According to aspects of the present invention, the sequence of at least one of the isolated nucleic acids which is attached to the test chamber (or portion thereof) encodes a promoter which is operatively linked to a nucleic acid sequence encoding a polypeptide.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter.

A "constitutive" promoter is a promoter that is active under most environmental and developmental conditions. An example of a constitutive promoter is cytomegalovirus (CMV) or Rous sarcoma virus (RSV) promoter.

An "inducible" promoter is a promoter that is active under environmental or developmental regulation.

Examples of inducible promoters include the tetracycline-inducible promoter (Srour, M. A., et al., 2003. Thromb. Haemost. 90: 398-405), an IPTG inducible promoter, P70, P70$_b$, P$_{28}$, P$_{38}$ or Plac\arac (P$_{la}$).

In the isolated nucleic acid, the promoter is preferably positioned approximately the same distance from the heterologous transcription start site as it is from the transcription start site in its natural setting. As is known in the art, however, some variation in this distance can be accommodated without loss of promoter function.

A DNA segment such as an expression control sequence is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a pre-protein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters, linkers, or PCR fragments by means know in the art.

According to one embodiment, the promoter is a eukaryotic promoter.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

According to another embodiment, the promoter is a prokaryotic promoter.

According to yet another embodiment, the promoter is a plant-specific promoter.

According to still another embodiment, the promoter is a tissue specific promoter.

The nucleic acid of this aspect of the present invention may further comprise an enhancer element. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences may also be present in the nucleic acids in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

The nucleic acid of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

In the context of this invention, the term "translational initiator sequence" is defined as the ten nucleotides immediately upstream of the initiator or start codon of the open reading frame of a DNA sequence coding for a polypeptide. The initiator or start codon encodes for the amino acid methionine. The initiator codon is typically ATG, but may also be any functional start codon such as GTG, TTG or CTG.

According to a particular embodiment, the nucleic acid of the present invention encodes an operon.

It will be appreciated that the individual elements comprised in the nucleic acid can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the nucleic acid, alternative configurations of the coding sequence within the nucleic acid are also envisioned.

In a particularly preferred embodiment of the invention, the nucleic acid molecule comprises a coding sequence coding for a predetermined amino acid sequence that is to be expressed.

According to one embodiment, at least one of the nucleic acids attached to the test chamber encodes a transcription factor, an activator or a repressor.

According to another embodiment, at least one of the nucleic acids attached to the test chamber encodes a polypeptide comprising a detectable moiety.

According to still another embodiment, the polypeptides are fluorescent polypeptides. Examples of such include, but are not limited to green fluorescent protein from *Aequorea*

*victoria* ("GFP"), the yellow fluorescent protein and the red fluorescent protein and their variants (e.g., Evrogen).

According to still another embodiment, the polypeptides are phosphorescent polypeptides, chemiluminescent polypeptides or luminescent polypeptides.

Table 1 provides non-limiting examples of such detectable moieties contemplated by the present invention.

TABLE 1

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR (SEQ ID NO: 2) | |
| orange fluorescent protein | AAL33917 | AF435432 |
| Beta galactosidase | ACH42114 | EU626139 |
| Streptavidin | AAM49066 | AF283893 |

It will be appreciated that a single test chamber may be attached to isolated nucleic acids each having the same sequence. Alternatively, a single test chamber may be attached to a plurality of isolated nucleic acids having different sequences. For example, a single test chamber may be attached to a plurality of isolated nucleic acids encoding a transcriptome.

Once the component is immobilized on the surface of the test chamber, the microfluidic device is preferably sealed using methods which are well known in the art. Low fluorescence adhesives which provide sealing and cover constructions may be used. Such adhesives are dimensionally stable and do not flow into microfluidic channels. They adhere to the cover layer without creating voids or gaps that may allow migration of components from one path to adjacent path, and they exhibit good stability to moisture and temperature change. Adhesives used in accordance with the present invention can be either flexible or rigid, but should preferably be clear and colorless (such adhesives can be obtained from Adhesives Research Inc.). Other adhesives include, but are not limited to, pressure sensitive adhesives, such as ethylene-containing polymers, urethane polymers, butyl rubber, butadiene-acrylonitrile polymers, butadiene-acrylonitrile-isoprene polymers, and the like. See, for example, U.S. Pat. No. 5,908,695 and references cited therein.

The fluid which carries/contains the non-immobilized components are typically buffered solutions which are physiologically relevant such that they do not interfere with the biological process—i.e. for the interaction between the components to take place.

The non-immobilized components are selected according to the biological process being carried out and the identity of the component immobilized to the test chamber surface.

Thus, for example when the biological process is transcription, the immobilized component may be DNA and the non-immobilized components may include ribonucleotides, RNA polymerase (e.g. RNA polymerase II) and transcription factors.

When the biological process is RNA translation, the immobilized component may be RNA and the non-immobilized components may include ribosomes, tRNA and amino acids.

When the biological process is gene expression (i.e. DNA to protein), the immobilized component may be DNA and the non-immobilized components may include ribonucleotides, RNA polymerase (e.g. RNA polymerase II), transcription factors, ribosomes, tRNA and amino acids.

When the biological process is protein modification, the immobilized component may be DNA and the non-immobilized components may include an enzyme that carries out the modification such as kinases; capping enzymes including phosphatases, guanosyl transferase, (guanine-$N^7$-)-methyltransferase etc.

Preferably, the non-immobilized components of this aspect of the present invention do not include DNA.

In one embodiment, a cell-free protein expression system is used in the method to provide the non-immobilized components. In a particular embodiment, a cell-free expression system is flowed through the microfluidic device of the present invention such that the non-immobilized components reach the test chamber and carry out the biological process.

An electric field gradient is then applied in the vicinity of the test chamber at a frequency which draws at least one non-immobilized component of the biological process away from the immobilized component towards the source of the electric field gradient.

Non-immobilized components of the biological process that may be drawn away from the immobilized component include the starting components used in the reaction and also intermediate products of the reaction (for example in the case of gene expression, a non-immobilized component may be RNA).

Electrodes may be used to apply an electric field gradient electrodes. The electrodes are used to use apply dielectrophoresis (DEP) to polarize and trap the non-immobilized components of the biological process.

The electrodes of the present invention may be fabricated from a metal such as platinum or gold. The electrodes are typically between 0.1-20 µm in width. The electrode may be of any shape, e.g. rectangular. In one embodiment, it is tapered.

The electrodes are typically in contact with the fluid inside the test chamber. Typically, the electrodes are placed at least 1 µm from the immobilized component in the test chamber. In another embodiment, the electrodes are placed between 1-50 µm from the immobilized component in the test chamber—e.g. about 10 µm.

According to a particular embodiment, the electrodes are between 0.1-30 µm apart.

In one embodiment, the electrodes are integrated into the microfluidic device i.e. are fashioned into the microfluidic device. The electrodes may be connected to a programmable voltage controller for applying desired voltage differentials.

Typically, the electric field gradient is generated using an AC electric potential of between 1 V-20 V, more preferably between 1 V-10 V (although higher or lower voltages are also contemplated).

The voltage may be selected such that a particular non-immobilized component is trapped. For example, the present inventors showed that at an applied Vpp=8, RNAP would be trapped but not ribosomes.

Selection of particular voltages for trapping all or a particular non-immobilized component of the reaction may be carried out by one of skill in the art as further described in the Examples section herein below.

The frequency of the electric field gradient is typically above the diffusion rate of ions—e.g. between 0.1-10 MHz.

In a particular embodiment, an AC electric potential of $10V_{pp}$ is applied at 1 MHz frequency.

The electric field gradient may be applied for any time—for example between 0.01 second—1 hour, more preferably between 1 second and 1 hour and even more preferably between 1 minute and 1 hour. According to an exemplary embodiment, the time for applying the electric field gradient is about 5-10 minutes.

The electric field gradient may be switched on and off intermittently to start and stop the biological process. The present invention contemplates providing additional non-immobilized components in order to restart the biological process. In another embodiment, no additional non-immobilized components are necessary to restart the biological process.

The present invention contemplates a myriad of application for the device and methods described herein, some of which are detailed herein below.
1. A biochip platform for research and development in areas such as systems and synthetic biology, biomedical diagnostics, high-throughput screening, protein expression system;
2. Biological assays in the context of gene expression in spatially defined on-chip reactor systems;
3. A biochip reactor platform for large-scale biosynthesis of molecules (proteins, RNA, peptides, hormones, etc.) with medical applications (e.g. Insulin) based on enzymatic reactions which are currently carried out in bacteria/plants;
4. A platform for embedding schemes of molecular computation in spatially arranged reactors on the chip; and
5. High-throughput analysis of protein functionality resulting from genetic mutations/variations. For example, after mutations/variations in a human genome have been detected, our chip could analyze whether this mutations lead to functionality loss of the expressed protein.

The following describes a simple configuration of one embodiment of the microfluidic device of the present invention, which can be utilized to control gene transcription/expression. It should be understood that this configuration is exemplary and that modifications thereof will be apparent to those skilled in the art.

FIG. 16 is a schematic illustration of a top view of a microfluidic device 10, according to various exemplary embodiments of the present invention. In a simple configuration, microfluidic device 10 comprises a test chamber 12, a stimulation chamber 16 and a microchannel 14. The stimulation chamber 16 is in fluid connection with the test chamber 12. Electrodes 34 are integrated into device 10 such that when current flows, an electric field potential is set up between the test chamber 12 and the stimulation chamber 16. The maximal field intensity of the electric field gradient is localized at least 1-50 μm from the test chamber 12.

Nucleic acids 18 are attached to the test chamber 12. The microchannel 14 is in communication with the flow-through channel 20.

Device 10 can also comprise an inlet port 26 which is in fluid communication with an external reagent inlet reservoir 22 such as by tubing (such as for infusing the reactants of the reaction) and an outlet port 28 which optionally may be in fluid communication with an outlet reservoir 30.

Fluids may be passively or actively infused into the flow channels such as by capillary forces or via a pump (e.g., external pumps, e.g., peristaltic pumps or electro-osmotically pumps). The device may be covered by a solid cover layer.

FIG. 17 is a schematic illustration of a top view of an additional microfluidic device 100, according to various exemplary embodiments of the present invention. In a simple configuration, microfluidic device 100 comprises a test chamber 120, and a microchannel 140. Electrodes 160 are integrated into device 100 such that when current flows, an electric field potential is set up between the outer area of the test chamber 120 and the inner area of the test chamber (the area where nucleic acids 180 are attached). The maximal field intensity of the electric field gradient is localized at least 1-50 μm from the inner area of the test chamber.

Nucleic acids 180 are attached to the test chamber 120. The microchannel 140 is in communication with the flow-through channel 200.

It will be appreciated that the device may comprise additional reaction units (a reaction unit being a test chamber connected to a microchannel). Optionally, each of the microchannels of the reaction units of the device are of the same length. In another embodiment, the length of at least one of the microchannels of the reaction units is different to the length of another microchannel of the reaction unit.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Fabrication of the Microfluidic Device

The compartment and main feeding channel (FIG. 1A, FIG. 4) were patterned on a silicon wafer (Si <100> 4", R>10,000 ohm/cm) in two UV-photolithography steps using a maskless laser write system (μPG 101, Heidelberg Instruments). The two layers were etched using Reactive Ion Etching (ICP-RIE, Surface Technology Systems, New Port, England). The compartments were first etched to a depth of 3 μm, and the main channel was then etched to a depth of 30 μm. Inlets and outlets of each device were drilled through (TBM 220, Proxxon; Dremel, 7103 diamond wheel point drill). The device was coated with a ~50 nm $SiO_2$ layer on both sides deposited by plasma enhanced chemical vapor deposition (Plasma-Therm VERSALINE, Saint Petersburg, Florida, USA).

Deposition of gold electrodes: Electrodes were patterned using a layer of liftoff resist (LOR10B, microchem) coated with a $2^{nd}$ layer of S1805 positive resist to create a thin 1 μm undercut on two substrates, compartment wafer coated with 50 nm of $SiO_2$, and fused silica (U.Q.G. optics, UV fused silica plates spectrosil 2000). Gold was evaporated to a thickness of 100 nm on top of 5 nm of chromium (Selen 500 Electron Beam source System, manufactured by Odem Scientific Application LTD). Liftoff was done using PG-remover at 50° C. The devices were cleaned and coated with a photoactive biocompatible monolayer [Buxboim, A. et al. Small 3, 500-10 (2007)] described in the following section.

DNA Brush assembly: Reactive amine groups of the biocompatible monolayer[5] were exposed to UV light from a laser source (μPG 101, Hidelberg instruments). Biotin N-hydroxysuccinimidyl ester (biotin-NHS) dissolved in a borate buffered saline (0.5 mg/ml) was incubated on the chip for 10 minutes. The biotin-NHS covalently attached to the exposed amine groups on the UV exposed monolayer attaining a surface pattern with biotin. Linear double strands of DNA fragments were produced by polymerase chain reaction with KAPA HiFi HotStart ReadyMix (KK2601, KAPA BIOSYSTEMS), using one primer with biotin and another with Alexa Fluor 647, both attached at the 5'-end (IDT). The final DNA solution contained Streptavidin (SA) conjugated DNA at a concentration of 150-300 nM in a phosphate buffered saline. Nano-liter DNA-SA droplets were individually deposited onto the reactor chambers using the GIX Microplotter II (Sonoplot Inc., Middleton, WI).

Antibodies and GFP assembly to the surface: 500 nM (~50 mg/ml) Anti-HA-Biotin, (High Affinity, 3F10 clone, Roche) was mixed with 2:1 amount of streptavidin (Sigma Aldrich) in PBS. After 30 minutes incubation at 4° C., to allow full formation of antibody-SA conjugates, and the mix was diluted to 25-50 nM in PBS and applied to the surface. The antibody-SA conjugate was incubated on the surface for 1 hour before repeated washing in PBS. Purified GFP fused to an HA tag were incubated on the surface for 15 minutes. The surface was washed and kept in PBS before the cell-free reaction was added.

Device sealing: The microfluidic device was sealed with a coverslip coated with PDMS. Magnets embedded in PDMS were punched and placed on the drilled holes of the device. Electrodes were connected to a waveform generator (Keysight, 33500B). PBS was continuously provided through the main flow channel, and then exchanged by a PURE cell-free reaction (CosmoBio, PUREfrex kit). The device was incubated at a temperature of 37° C., with the PURE reaction reservoir incubated at 4° C. close to the device.

Assembly of PDMS well: Circular holes of ~1.5 mm radius were cut through a 250 μm thin and flat PDMS sheet. The PDMS was aligned to gold electrodes evaporated on the fused silica surface (FIG. 2A). Nano-liter DNA-SA droplets were individually deposited onto the fused silica surface next to the tips of the electrodes as described for the microfluidic chip. The DNA solution was washed, and the fused silica slide assembled on a prism as described previously [Bracha, D. & Bar-Ziv, R. H. *J. Am. Chem. Soc.* 136, 4945-4953 (2014)]. Electrodes were connected the waveform generator. The well was filled with the PURE cell-free reaction, sealed with a 5 mm diameter coverslip, and incubated at 37° C. Experiments done in the PDMS well typically lasted 30 min before depletion of nutrients and termination of the reaction.

Labeled RNAP, RNA and Ribosomes:

Labeling and purification of eGFP-T7 RNAP. The gene coding for eGFP was cloned into plasmid pBH161 [He, B. et al. Protein Expr. Purif. 9, 142-151 (1997)] under control of the *E. coli* UV5 promoter and upstream of the ATG codon of the T7 RNAP gene. The resulting protein His6-eGFP-T7RNAP was over-expressed in BL21(DE3) cells after induction with 1 mM IPTG at $OD_{600}$ of 0.5 for 3 hrs and purified using conventional protocols. Briefly, the protein was first purified by $Ni^{2+}$ affinity chromatography using 2×1 ml HisTrap FF columns (GE healthcare). Fractions containing appreciable absorbance at 488 nm, eluted at 90 mM imidazole, were pooled and concentrated using vivaspin 20 MWCO 10 kDa (Sartorius). Following buffer exchange to 10 mM Tris-HCl pH 7.5; 100 mM NaCl, the sample was loaded onto superdex200 (GE healthcare) gel filtration column. Fractions containing appreciable absorbance at 488 nm were pooled and concentrated using vivaspin 20 MWCO 10 kDa (Sartorius). Purified His6-eGFP-T7RNAP was stored at −80° C. in 50 mM Tris pH 7.5; 100 mM NaCl; 10 mM DTT at a concentration of 50 μM and added to a PUREfrex Tx/Tl reaction (Cosmo Bio Ltd. Japan) at a concentration of 700 nM.

Labeling and purification of *E. coli* ribosomes. eGFP coding sequence was cloned at the C-terminus of ribosomal protein S15. The S15-eGFP gene fusion was inserted into plasmid pRSFduet under control of T7 promoter/lac operator. S15-eGFP was over-expressed in BL21(DE3) by induction with 1 mM IPTG at $OD_{600}$ of 0.5 for 3 hrs. Cell lysis and ribosome purification were performed essentially as previously described [Trauner, A., et al., *PLoS One* 6, e16273 (2011)] using 1 ml quaternary amine monolith column (CIMmultusTM QA-1 ml, BIA separations). Fractions eluting at 350 mM NaCl were pooled, concentrated to 8 μM using vivaspin 20 MWCO 10 kDa (Sartorius) with buffer exchange to Tris-HCL pH 7.5; 70 mM KCl; 10 mM $MgCl_2$. Labeled ribosomes were stored at −80° C. and added to PURE Tx/Tl reaction at a final concentration of 700 nM.

In vitro synthesis and labeling of *E. coli* 16S rRNA. *E. coli* 16S rRNA gene lacking its leader sequence was cloned under control of the T7 promoter in the PUREfrex control plasmid (Cosmo Bio, Japan) replacing the DHFR gene. A broccoli aptamer [Filonov, G. S et al doi:10.1021/ja508478x] was cloned in the loop sequence of helix 6 of the 16S rRNA gene: gtcgaacggtaacaggaagaagctGCGGA-GACGGTCGGGTCCAGATATTCGTATCTGTC GAGTAGAGTGTGGGCTCCGCtgcttctttgctgacgagtggc (SEQ ID NO: 1; Capital letters Broccoli aptamer; small letters Helix 6 sequence). The 16S-H6-Broccoli rRNA was synthesized in a PUREfrex Tx/Tl reaction and visualized by the addition of DHFBI-1T (Lucerna, Inc, TM NY) at a final concentration of 30 μM.

Numerical Model:

We describe a numerical solution considering depletion of machinery by a pulse of electric field in the DNA compartment (model solved in Matlab using ODE45). The compartments were patterned with a DNA construct encoding for GFP expressed under T7 promoter, $P_{T7}$-GFP. Messenger RNA (mRNA; m) is constitutively transcribed and then translated into GFP (p). The diffusion of RNA polymerase (RNAP; $r_p$) and ribosome ($R_b$) from the feeding channel into the compartment is taken into account. We assume for simplicity that the E-field completely depletes biomolecules from further activity, which we model by a theta function: $\Theta(E>0)=1$ when the field in ON, and $\Theta(E=0)=0$, when the field is OFF. The transcription-translation reaction in the compartment was modeled by four coupled effective differential equations:

$$\frac{dr_p}{dt} = \frac{r_0 - r_p}{\tau_{rp}} - \frac{r_p \cdot \Theta(E)}{\tau_E} \quad (1)$$

$$\frac{dR_b}{dt} = \frac{R_0 - R_b}{\tau_{Rb}} - \frac{R_b \cdot \Theta(E)}{\tau_E} \quad (2)$$

$$\frac{dm}{dt} = k_{TX} \cdot D \cdot r_p - \frac{m}{\tau_m} \quad (3)$$

$$\frac{dp}{dt} = k_{TL} \cdot R_b \cdot m - \frac{p}{\tau_p} \quad (4)$$

The parameter values can be found in Table 2. Equation (1) describes the kinetics of $r_p$ in the compartment, with $r_0$ the bulk concentration in the feeding channel, $\tau_{rp}$ is the diffusion time into and out of the compartment, and $\tau_E$ is the response time to the electric field. For $\tau_E \ll \tau_{rp}$ the second term of the right-hand side of the equation is dominant, and the diffusion rate of $r_p$ in the compartment drops to zero $$\frac{dr_p}{dt} \to 0.$$

Equation (2) describes the diffusion of ribosomes into the compartment, with $R_0$ is the bulk concentration in the feeding channel, $\tau_{Rb}$ is the diffusion time of $R_b$ into and out of the compartment. Similarly, as in equation (1) For $\tau_E \ll \tau_{Rb}$ the concentration of ribosomes drops to zero in the compartment, $$\frac{dr_p}{dt} \to 0$$

when the E-field is applied. Equation (3) describes the kinetics of m, with transcription rate, $k_{TX}$, DNA concentration, D, and mRNA lifetime $\tau_m$. Equation (4) describes the kinetics of protein expression in the compartment with translation rate, $k_{TL}$, the, and protein lifetime $\tau_p$. The E-field, modeled by $\Theta(E)$, was applied separately to $r_p$, $R_b$, M, p, in Eqs. 1-4 and the resulting dynamics was simulated (FIG. 6). The results are most compatible with the depletion of both ribosome and RNAP.

TABLE 2 parameters taken in the numerical solution-Values are taken from J. Biosci. Bioeng. 118, 554-557 (2014); and Karzbrun, E., et al., Science 345, 829-832 (2014)

| | |
|---|---|
| TX—Transcription rate | $0.1 \left[\frac{1}{\min}\right]$ |
| TL—Translation rate | $0.8 \left[\frac{1}{\min}\right]$ |
| $r_0$—RNAP concentration in extract | 0.5 [μM] |
| $R_0$—Ribosomes concentration in extract | 1 [μM] |
| $k_{TX} = \frac{TX}{r_0}$ | |
| $k_{TL} = \frac{TL}{R_0}$ | |
| D—DNA concentration. | 100 [nM] |
| $\tau_E$—Response time to applied E-field. | 1-3 [min] |
| $\tau_{rp}$—RNAP diffusion time. | 30-50 [min] |
| $\tau_{Rb}$—Ribosomes diffusion time. | 40-60 [min] |
| $\tau_m$—mRNA lifetime. | 10-20 [min] |
| $\tau_p$—protein lifetime. | 20-30 [min] |
| Pulse duration of E field | 5-10 [min] |

Numerical simulation of E-field lines and dielectrophoresis (DEP): Finite element simulations (Comsol Multiphysics5.2) were used to solve Poisson's equation in the compartment, and determine the E-field (DC voltage) created by gold electrodes with an applied potential of $V=10V_{pp}$ (FIGS. 6 and 8). The simulated DC field value can be interpreted as the root mean square (RMS) value of the experimental AC field. In the simulation we took into account gold electrodes on an insulating silicon substrate immersed in an aqueous buffer with electric relative permittivity of PBS, $\varepsilon_r=77$, and conductivity $$\sigma = 1.5 \left[\frac{S}{m}\right].$$

The simulations were performed on 2D meshes. The DEP force field direction was derived from the gradient of the electrical field squared, $F \propto \nabla E^2$. The simulation showed that the direction of the DEP force field points toward the electrode tips, with a maximal amplitude of the field, $E=10^7$V/m, at the tips.

Results

To study the response of gene expression to an E-field, a reconstituted cell-free protein synthesis reaction based on purified components[25] (PURE system) was used. Cell-free systems[25-27] provide a means to study biological design principles by programming minimal gene networks to exhibit emergent spatiotemporal expression patterns[3,6,28-30]. To overcome the challenge of manipulating homogenously dispersed reaction components, the DNA code was immobilized as a dense brush, thereby breaking the symmetry and localizing the reaction close to the surface of a compartment. An E-field gradient applied to electrodes patterned close to the DNA brush creates a scenario for effectively perturbing the reaction by separating transcription-translation enzymes from the DNA code. At Mega-Hertz frequency, screening and electro-osmotic effects were overcome in a solution of high ionic strength[16,31] with conductivity of about ~1 S/m.

The DNA compartment was assembled as an artificial cell[6] by carving in silicon two overlapping circles of radius R=35 μm and depth of h=35 μm, which were connected to a large feeding channel through a capillary of width W=15 μm and length L=200 (FIGS. 1A and 4). The entire chip was coated with a 50 nm thin $SiO_2$ insulating layer, and two gold electrodes, 100 nm thin and d=15 μm apart, were evaporated on the upper surface of the chip at the upper compartment. The chip was then coated by a photoactivable monolayer, and linear DNA templates coding for GFP under a T7 promoter were patterned in the lower compartment. Once the chip was sealed, a PURE reaction was flown in the feeding channel, diffused into the compartment initiating mRNA transcription and protein synthesis. Continuous expression in the compartment and dilution of products out of the capillary maintained protein concentration at steady-state. The effective protein lifetime in the compartment was set by geometry and diffusion, $$\tau = \frac{2\pi R^2 L}{DW} \approx 45 \text{ min,}$$

with D=45 μm²/s the diffusion coefficient of GFP[6].

An AC electric potential of $10V_{pp}$ at 1 MHz frequency was applied between the electrodes connected to the DNA compartment, for a duration of 5 min. Upon application of the E-field, GFP concentration immediately dropped and continuously decreased reaching zero value within 20 minutes (FIG. 1B). GFP levels then gradually increased again at a rate comparable to the initial synthesis rate and continued for 60 min before another E-field application. This process was then repeated 4 times, creating E-field driven periodic pulses in protein concentration (FIG. 1B). The recovery time matched the compartment lifetime, $\tau$, suggesting complete depletion of machinery and products occurred throughout the E-field ON period (FIGS. 1B, 1C). Notably, the effect of E-field on gene expression was most pronounced in the compartment connected to the electrodes, and could be observed to a lesser extent as a function of distance of nearby compartments (FIG. 1D). The DNA remained intact bound to the surface throughout the experiment.

To explain the effect of the E-field in the compartment, the present inventors examined a scenario in which a pulse of DEP stops protein synthesis by depletion of biomolecules involved in the reaction, including RNA polymerase (RNAP) and ribosomes, the enzymatic machineries that synthesize the respective mRNA and GFP products. A numerical solution to a transcription-translation coupled differential equations (Eq.1-4), indicated that depletion of RNAP and ribosomes sufficiently captures the salient features of the dynamics (FIG. 1E, FIGS. 5A-F): (i) immediate drop in GFP concentration upon E-field application and rapid decrease due to machinery depletion within a few minutes; (ii) further drop in GFP after inactivation of E-field; (iii) slower recovery of GFP synthesis due to replenishment of machinery by diffusion from the capillary, over a timescale of $\tau$. The simulation also indicated that depletion of GFP, rather than machinery, cannot by itself reproduce the lag in recovery after inactivation of E-field (FIG. 6). The direction of the E-field gradient in the compartment was simulated as well, and was found to be consistent with attraction of biomolecules toward the region of highest field intensity close to the electrodes (FIG. 6).

To better understand the effect of E-field in the DNA compartment, the present inventors sought to directly measure the response of the key molecular components in a larger chamber, 250 μm deep and 3 mm wide, with electrodes d=10 μm apart on a fused silica insulating surface (FIG. 2A). The DEP force field perpendicular to the E-field was visualized by the streamlines of 1 μm beads in water, where the Joule heating and electro-osmosis at high ionic strength[31] is minimized, leaving DEP as main effect driving bead motion[32] (FIG. 2B, FIGS. 7A-D). The attraction of the beads to the maximal field intensity region between the electrodes is consistent with a numerical solution of the DEP force field (FIG. 8). Next, separate PURE protein-synthesis reactions were carried out, each supplemented with either a purified protein fusion of RNAP-GFP, ribosome-GFP, or GFP alone, each at 0.7 μM concentration. These fluorescently labeled molecules were imaged using Total Internal Reflection Fluorescence Microscopy (TIRFM) within a ~100 nm layer close to the surface between the electrodes. At f=1 MHz, V=10$V_{pp}$ attraction and accumulation of molecules between the electrodes was observed as the TIRFM signal increased continuously. Notably, the fluorescent signal between the electrodes, whether of ribosome-GFP, RNAP-GFP or GFP, did not decrease after the E-field had been turned off and stayed at a constant level (shown for RNAP-GFP in FIG. 18).

A significant fraction of the measured molecules attracted near the electrodes were adsorbed irreversibly (FIG. 2C).

Interestingly, the trapping rate as measured by the fluorescent accumulation near the electrodes, differed between biomolecules and did not scale with their size (FIG. 9). To understand which molecular property determined the attraction toward the electrodes, we measured the trapping rate as a function of the applied voltage, and observed an increase in rate with voltage beyond a sharp threshold value $V_{th}$ (FIG. 2D, FIG. 10). A hierarchy in $V_{th}$ was found, with RNAP-GFP responding at a lower threshold value than both ribosome-GFP and GFP alone (FIG. 2D). Using the values of $V_{th}$ the present inventors estimated the minimal dipolar energy, $½\alpha E_{th}^2$, required to balance the thermal energy, $3/2k_BT$, and calculated the induced polarizability in the reaction solution[19,33], $$\alpha = \frac{3k_BT}{E_{th}^2} \approx \frac{3k_BT d^2}{V_{th}^2} \approx 3.6 \cdot 10^{-32};$$

$2 \cdot 10^{-32}$; $1.4 \cdot 10^{-32}$ F·m² for RNAP-GFP, ribosome-GFP, and GFP, respectively (FIG. 11). These values are consistent with polarizability values obtained for ribosomal RNA[33], and plasmid DNA[34] at low ionic strength. Furthermore, the trapping rate at $10V_{pp}$ decreased linearly with $V_{th}^2$ (FIG. 2E) for the three different biomolecules, suggesting that DEP is the driving force for trapping, $F_{DEP}=½\alpha\nabla E^2 \propto 1/V_{th}^2$. Finally, molecular attraction near the electrodes is most likely determined by the induced polarizability rather than by size or molecular weight (FIG. 11), and $F_{DEP}$ was estimated as:

$$F_{DEP} \approx \frac{\alpha V^2}{d^3} \approx 10^{-15} N$$

(1 MHz, $10V_{pp}$). Additional experiments showed that the trapping rate decreased 10-fold as the distance between the electrodes varied from d=10 μm to 100 μm (FIG. 12), possibly suggesting long-range effects at large electrode distances.

Figure 3B:
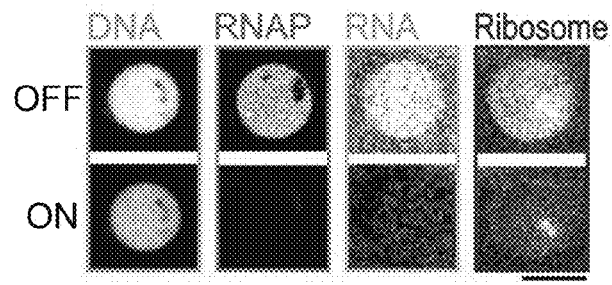

Next, the long-range response of gene expression in DNA brushes during application of an E-field were studied. DNA brushes coding for GFP were patterned on the surface along the symmetry axis of the E-field, up to 600 μm from the electrodes (FIG. 3A). Localized transcription-translation activity was detectable by TIRFM[35] as RNAP-GFP, ribosome-GFP, and newly synthesized RNA (labeled by a fluorescent probe[36]), all concentrated at the DNA brush (FIG. 3B). Non-coding DNA brushes, symmetrically patterned on the opposite side of the electrodes as background negative controls, did not exhibit localization of RNAP-GFP, RNA or ribosome-GFP (FIGS. 13A-C). The localized activity at a coding brush, 150 μm from the electrodes, decreased by more than two-fold relative to a noncoding brush, upon application of the E-field (1 MHz, $10V_{pp}$, for 1 min), with a concomitant accumulation of all the labeled molecules near the electrodes (FIG. 2C). As control experiments the present inventors measured that the direct effect of the E-field on the signals of both immobilized DNA and patterned GFP, was a minor decrease of ~15-25%, in contrast to the 2-fold effect on diffusible machinery (FIGS. 14A-D). These experiments demonstrated separation of the enzymatic machinery and synthesized RNA from coding DNA brushes due to attraction towards the electrodes.

Figure 3C:
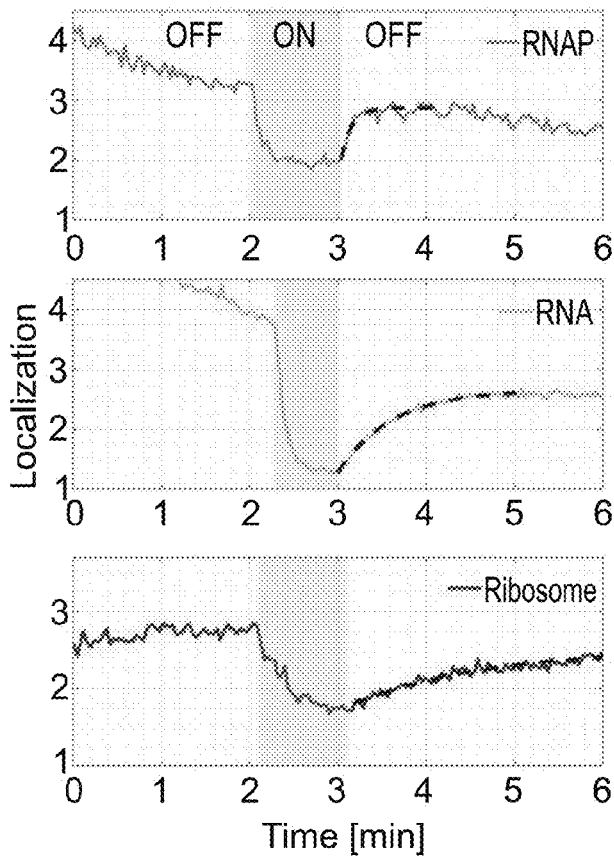
Figure 3D:
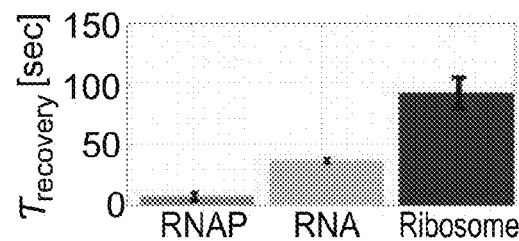
Figure 3E:
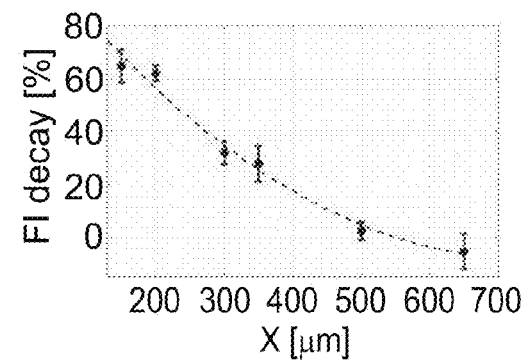
Figure 3F:
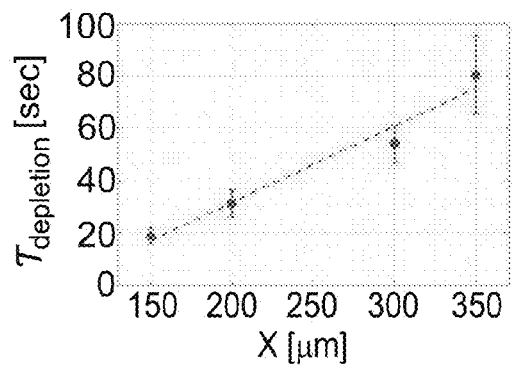

The hierarchy in response to the E-field of the biomolecules (FIGS. 2D-E), together with their different interaction with the DNA brush, motivated the present inventors to study the kinetics of depletion and recovery. A rapid 2-fold depletion of RNAP-GFP and ribosome-GFP from the active brush was observed within 20 sec and 45 sec, respectively, after E-field was turned on, followed by localization back to the brush within 10 sec and 90 sec, after E-field was turned off (FIGS. 3C-D). Newly synthesized RNA was also depleted by 2-fold within 20 sec and recovered over 40 sec. Surprisingly, despite the strong direct interaction of RNAP with the DNA, the force induced by the E-field seemed to be pulling it away from the DNA brush more readily than ribosome, possibly due to its higher polarizability (FIG. 2E). The slower recovery of ribosomes back to the brush is likely due to its indirect interaction with DNA coupled to nascent RNA that is bound to RNAP. Consistently with this scenario, the fluorescent signal of newly synthesized RNA appeared localized to the brush only after RNAP has relocalized to the brush (FIG. 3C). The effect of the localized E-field on gene-expression activity in a DNA brush was more pronounced closer to the electrodes, as apparent by reduced ribosome localization and faster depletion time in response to the E-field (FIGS. 3E-F).

In highly conductive aqueous solutions localized E-fields induce Joule heating that generate thermal gradients, resulting in long-range fluid motion[23,31]. To assay the spatial extent and magnitude of this electrothermal effect, purified GFP molecules were immobilized on a predetermined pattern in the vicinity of the electrodes and their standard fluorescence (insensitive to height) was measured in response to the E-field (FIG. 15). We noticed a drop of ~8% in GFP signal that is consistent with a temperature increase[37] of ~8° K, which persisted over a scale of ~250 μm. This suggests that electrothermal effects may lead to the long-range depletion of machinery from DNA brushes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Basu, S., Gerchman, Y., Collins, C. H., Arnold, F. H. & Weiss, R. A synthetic multicellular system for programmed pattern formation. *Nature* 434, 1130-4 (2005).
2. Danino, T., Mondragón-Palomino, O., Tsimring, L. & Hasty, J. A synchronized quorum of genetic clocks. *Nature* 463, 326-30 (2010).
3. Tayar, A. M., Karzbrun, E., Noireaux, V. & Bar-Ziv, R. H. Synchrony and pattern formation of coupled genetic oscillators on a chip of artificial cells. *Proc. Natl. Acad. Sci. U.S.A* 114, 11609-11614 (2017).
4. Brophy, J. A. N. & Voigt, C. A. Principles of genetic circuit design. *Nat. Methods* 11, 508-20 (2014).
5. Daniel, R., Rubens, J. R., Sarpeshkar, R. & Lu, T. K. Synthetic analog computation in living cells. *Nature* 497, 619-23 (2013).
6. Karzbrun, E., Tayar, A. M., Noireaux, V. & Bar-Ziv, R. H. Programmable on-chip DNA compartments as artificial cells. *Science* 345, 829-832 (2014).
7. Haellman, V. & Fussenegger, M. Synthetic biology— Engineering cell-based biomedical devices. *Curr. Opin. Biomed. Eng.* 4, 50-56 (2017).
8. Deiters, A. Light activation as a method of regulating and studying gene expression. *Curr. Opin. Chem. Biol.* 13, 678-686 (2009).
9. Levskaya, A., Weiner, O. D., Lim, W. A. & Voigt, C. A. Spatiotemporal control of cell signalling using a light-switchable protein interaction. *Nature* 461, 997-1001 (2009).
10. Booth, M. J., Schild, V. R., Graham, A. D., Olof, S. N. & Bayley, H. Light-activated communication in synthetic tissues. *Sci. Adv.* 2, (2016).
11. Mannix, R. J. et al. Nanomagnetic actuation of receptor-mediated signal transduction. *Nat. Nanotechnol.* 3, 36-40 (2008).
12. Dobson, J. Remote control of cellular behaviour with magnetic nanoparticles. *Nat. Nanotechnol.* 3, 139-143 (2008).
13. Tschirhart, T. et al. Electronic control of gene expression and cell behaviour in *Escherichia coli* through redox signalling. *Nat. Commun.* 8, 14030 (2017).
14. Shivashankar, G. V., Liu, S. & Libchaber, A. Control of the expression of anchored genes using micron scale heater. *Appl. Phys. Lett.* 76, 3638 (2000).
15. Kreysing, M., Keil, L., Lanzmich, S. & Braun, D. Heat flux across an open pore enables the continuous replication and selection of oligonucleotides towards increasing length. *Nat. Chem.* 7, 203-208 (2015).
16. Bazant, M. Z., Thornton, K. & Ajdari, A. Diffuse-charge dynamics in electrochemical systems. *Phys. Rev. E* 70, 21506 (2004).
17. Pohl, H. A. *Dielectrophoresis: the behavior of neutral matter in nonuniform electric fields*. (Cambridge University Press, 1978).
18. Nakano, A. & Ros, A. Protein dielectrophoresis: Advances, challenges, and applications. *Electrophoresis* 34, 1085-1096 (2013).
19. Tuukkanen, S. et al. Trapping of 27 bp-8 kbp DNA and immobilization of thiol-modified DNA using dielectrophoresis. *Nanotechnology* 18, 295204 (2007).
20. Hölzel, R., Calander, N., Chiragwandi, Z., Willander, M. & Bier, F. F. Trapping Single Molecules by Dielectrophoresis. *Phys. Rev. Lett.* 95, 128102 (2005).
21. Castellanos, A., Ramos, A., Gonzalez, A., Green, N. G. & Morgan, H. Electrohydrodynamics and dielectrophoresis in microsystems: scaling laws. *J. Phys. D. Appl. Phys.* 36, 2584-2597 (2003).
22. Nili, H. & Green, N. G. in *Encyclopedia of Nanotechnology* 1-10 (Springer Netherlands, 2015). doi:10.1007/978-94-007-6178-0_130-2
23. Chaurey, V., Polanco, C., Chou, C.-F. & Swami, N. S. Floating-electrode enhanced constriction dielectrophoresis for biomolecular trapping in physiological media of high conductivity. *Biomicrofluidics* 6, 12806 (2012).
24. Gao, J. et al. Hybrid electrokinetic manipulation in high-conductivity media. *Lab Chip* 11, 1770-5 (2011).
25. Shimizu, Y. et al. Cell-free translation reconstituted with purified components. *Nat. Biotechnol.* 19, 751-755 (2001).
26. Noireaux, V., Bar-Ziv, R. & Libchaber, A. Principles of cell-free genetic circuit assembly. *Proc Natl Acad Sci USA* 100, 12672-12677 (2003).
27. Shin, J. & Noireaux, V. An *E. coli* cell-free expression toolbox: application to synthetic gene circuits and artificial cells. *ACS Synth. Biol.* 1, 29-41 (2012).
28. Noireaux, V. & Libchaber, A. A vesicle bioreactor as a step toward an artificial cell assembly. *Proc Natl Acad Sci USA* 101, 17669-74 (2004).
29. Niederholtmeyer, H., Stepanova, V. & Maerkl, S. J. Implementation of cell-free biological networks at steady state. *Proc. Natl. Acad. Sci. U.S.A* 110, 15985-90 (2013).
30. Hansen, M. M. K. et al. Macromolecular crowding creates heterogeneous environments of gene expression in picolitre droplets. *Nat. Nanotechnol.* 11, 191-197 (2015).
31. Morgan, H. & Green, N. G. *AC electrokinetics: colloids and nanoparticles*. (Research Studies Press, 2003).
32. Ermolina, I. & Morgan, H. The electrokinetic properties of latex particles: comparison of electrophoresis and dielectrophoresis. *J. Colloid Interface Sci.* 285, 419-428 (2005).
33. Giraud, G. et al. Dielectrophoretic manipulation of ribosomal RNA. *Biomicrofluidics* 5, 24116 (2011).
34. Suzuki, S., Yamanashi, T., Tazawa, S., Kurosawa, O. & Washizu, M. Quantitative analysis of DNA orientation in stationary AC electric fields using fluorescence anisotropy. *IEEE Trans. Ind. Appl.* 34, 75-83 (1998).
35. Bracha, D., Karzbrun, E., Daube, S. S. & Bar-Ziv, R. H. Emergent Properties of Dense DNA Phases toward Artificial Biosystems on a Surface. *Acc. Chem. Res.* 47, 1912-1921 (2014).
36. Filonov, G. S., Moon, J. D., Svensen, N. & Jaffrey, S. R. Broccoli: Rapid Selection of an RNA Mimic of Green Fluorescent Protein by Fluorescence-Based Selection and Directed Evolution. doi:10.1021/ja508478x
37. Nakano, M. et al. Genetically encoded ratiometric fluorescent thermometer with wide range and rapid response. *PLoS One* 12, e0172344 (2017).

What is claimed is:

1. A method of controlling a biological process in a test chamber of a microfluidic device, which comprises:
   (i) at least one reaction unit having a test chamber connected to at least one microchannel, wherein a surface of at least a portion of said test chamber is attached to an immobilized component of a biological process;
   (ii) a flow-through channel having at least one inlet port and at least one outlet port, said flow-through channel being connected to said reaction unit via said at least one microchannel;
   (iii) a stimulation chamber which is connected to said test chamber; and
   (iv) two electrodes patterned into said device being in physical contact with said stimulation chamber, said two electrodes being at least 1-50 µm from said test chamber,
   wherein the method comprises:
      (a) providing non-immobilized components of the biological process to the microfluidic device under conditions that allow said non-immobilized components to reach said test chamber; and
      (b) applying an electric field gradient in the vicinity of said test chamber at a frequency which draws at least one non-immobilized component of said biological process away from said immobilized components towards a source of said electric field gradient, thereby controlling the biological process.

2. The method of claim 1, wherein the biological process is DNA transcription, gene expression or protein modification.

3. The method of claim 1, wherein said immobilized component is a nucleic acid.

4. The method of claim 1, wherein said applying said electric field gradient is effected between 0.01 second and 1 hour.

5. The method of claim 1, further comprising terminating said electric field gradient.

6. The method of claim 1, wherein said frequency is between 0.1-10 MHz.

7. The method of claim 1, wherein the controlling comprises stopping and restarting.

* * * * *

SEQUENCE LISTING

<160> NUMBER OF SEQ ID NOS: 2

<210> SEQ ID NO 1
<211> LENGTH: 101
<212> TYPE: DNA
<213> ORGANISM: Artificial Sequence
<220> FEATURE:
<223> OTHER INFORMATION: The 16S-H6-Broccoli rRNA

<400> SEQUENCE: 1
gtcgaacggt aacaggaaga agctgcggag acggtcgggt ccagatattc gtatctgtcg    60
agtagagtgt gggctccgct gcttctttgc tgacgagtgg c                        101

<210> SEQ ID NO 2
<211> LENGTH: 15
<212> TYPE: PRT
<213> ORGANISM: Artificial Sequence
<220> FEATURE:
<223> OTHER INFORMATION: Biotin lygase tag

<400> SEQUENCE: 2

Leu His His Ile Leu Asp Ala Gln Lys Met Val Trp Asn His Arg
1               5                   10                  15